(12) United States Patent
Dai et al.

(10) Patent No.: US 11,337,982 B2
(45) Date of Patent: May 24, 2022

(54) COMBINED TREATMENT WITH A TLR7 AGONIST AND AN HBV CAPSID ASSEMBLY INHIBITOR

(71) Applicant: Hoffmann-La Roche Inc., Little Falls, NJ (US)

(72) Inventors: Lue Dai, Shanghai (CN); Lu Gao, Shanghai (CN)

(73) Assignee: Hoffmann-La Roche, Inc., Little Falls, NJ (US)

( * ) Notice: Subject to any disclaimer, the term of this patent is extended or adjusted under 35 U.S.C. 154(b) by 0 days.

(21) Appl. No.: 16/351,922

(22) Filed: Mar. 13, 2019

(65) Prior Publication Data

US 2019/0298726 A1 Oct. 3, 2019

Related U.S. Application Data

(63) Continuation of application No. PCT/EP2017/072671, filed on Sep. 11, 2017.

(30) Foreign Application Priority Data

Sep. 13, 2016 (WO) ................ PCT/CN2016/098892

(51) Int. Cl.
| | | |
|---|---|---|
| *A61K 31/522* | (2006.01) | |
| *A61K 31/506* | (2006.01) | |
| *A61K 31/4985* | (2006.01) | |
| *A61K 31/513* | (2006.01) | |
| *A61K 31/675* | (2006.01) | |

(Continued)

(52) U.S. Cl.
CPC ........ *A61K 31/522* (2013.01); *A61K 31/4985* (2013.01); *A61K 31/506* (2013.01); *A61K 31/513* (2013.01); *A61K 31/675* (2013.01); *A61K 45/06* (2013.01); *A61P 31/20* (2018.01)

(58) Field of Classification Search
CPC ..... A61K 31/522; A61K 31/506; A61K 45/06
See application file for complete search history.

(56) References Cited

U.S. PATENT DOCUMENTS

| 7,642,350 B2 | 1/2010 | Pryde et al. |
| 2007/0072934 A1 | 3/2007 | Congxin et al. |
| 2010/0143301 A1 | 6/2010 | Desai et al. |

(Continued)

FOREIGN PATENT DOCUMENTS

| CN | 101239980 A | 8/2008 |
| CN | 104650069 A | 5/2015 |

(Continued)

OTHER PUBLICATIONS

Funk et al, Journal of Translational Medicine 2014, vol. 12(129), pp. 1-8. (Year: 2014).*

(Continued)

*Primary Examiner* — Craig D Ricci
*Assistant Examiner* — Janet L Coppins
(74) *Attorney, Agent, or Firm* — Genentech, Inc.; Richard G. A. Bone

(57) ABSTRACT

The present invention is directed to compositions and methods for treating hepatitis B virus infection. In particular, the present invention is directed to a combination therapy comprising administration of a TLR7 agonist and an HBV capsid assembly inhibitor for use in the treatment of chronic hepatitis B patient.

14 Claims, 6 Drawing Sheets

Specification includes a Sequence Listing.

(51) Int. Cl.
  *A61K 45/06* (2006.01)
  *A61P 31/20* (2006.01)

(56) References Cited

U.S. PATENT DOCUMENTS

| | | |
|---|---|---|
| 2011/0150836 A1 | 6/2011 | Halcomb et al. |
| 2014/0275167 A1 | 9/2014 | Hartman et al. |

FOREIGN PATENT DOCUMENTS

| | | |
|---|---|---|
| DE | 100 13 126 A1 | 9/2001 |
| JP | 11-193282 A | 7/1999 |
| TW | 201546075 A | 12/2015 |
| WO | 01/68642 A1 | 9/2001 |
| WO | 2005/085462 A1 | 9/2005 |
| WO | 2006/033995 A2 | 3/2006 |
| WO | 2006/033995 A3 | 3/2006 |
| WO | 2006/117670 A1 | 11/2006 |
| WO | 2008/004948 | 1/2008 |
| WO | 2008/090115 A1 | 7/2008 |
| WO | 2009/067547 A1 | 5/2009 |
| WO | 2009/103176 A1 | 8/2009 |
| WO | 2010/023480 A1 | 3/2010 |
| WO | 2010/069147 A1 | 6/2010 |
| WO | 2012/019426 A1 | 2/2012 |
| WO | 2013/096744 A1 | 6/2013 |
| WO | 2013/144129 A1 | 10/2013 |
| WO | 2014/037480 A1 | 3/2014 |
| WO | 2014/184328 A1 | 11/2014 |
| WO | 2015/132276 A1 | 9/2015 |
| WO | 2016/023511 A1 | 2/2016 |
| WO | 2016/146598 A1 | 9/2016 |
| WO | 2016/180695 A1 | 11/2016 |

OTHER PUBLICATIONS

Cho et al, Journal of Viral Hepatitis 2014, vol. 21, pp. 843-852. (Year: 2014).*
Allan et al., "Synthesis of analogs of GABA .15. preparation and resolution of some potent cyclopentene and cyclopentane derivatives" Aust. J. Chem 39:855-64 ( 1986).
Brezillon et al., "Antiviral activity of Bay 41-4109 on hepatitis B virus in humanized Alb-uPA/SCID mice" PLoSONE 6(12 SUPPL 1-6):e25096 (Dec. 2011).
Deres et al., "Inhibition of hepatitis B virus replication by drug-induced depletion of nucleocapsids" Science 299(5608):893-6 ( 2003).
Feld et al., "The phenylpropenamide derivative AT-130 blocks HBV replication at the level of viral RNA packaging" Antiviral Res 76:168-177 ( 2007).
Grygorenko et al., "Expedient synthesis of cis- and trans-3-aminocyclobutanecarboxylic acids" Synthetic Communications 41:1644-1649 ( 2011).
Guo et al., "Characterization of the intracellular deproteinized relaxed circular DNA of hepatitis B virus: an intermediate of covalently closed circular DNA formation" J Virol 81:12472-12484 ( 2007).
"International Preliminary Report on Patentability—PCT/EP2017/072671":1-8 (dated Mar. 19, 2019).
"International Search Report—PCT/EP2017/072671":1-17 (dated Nov. 22, 2017).
Sandstroem et al., "B-Amino acid substitutions and structure-based CoMFA modeling of hepatitis C virus NS3 protease inhibitors" Bioorgan Med Chem 16:5590-5605 ( 2008).
Zlotnick et al., "A small molecule inhibits and misdirects assembly of hepatitis B virus capsids" J Virol 76(10):4848-4854 (May 2002).

* cited by examiner

A.

B

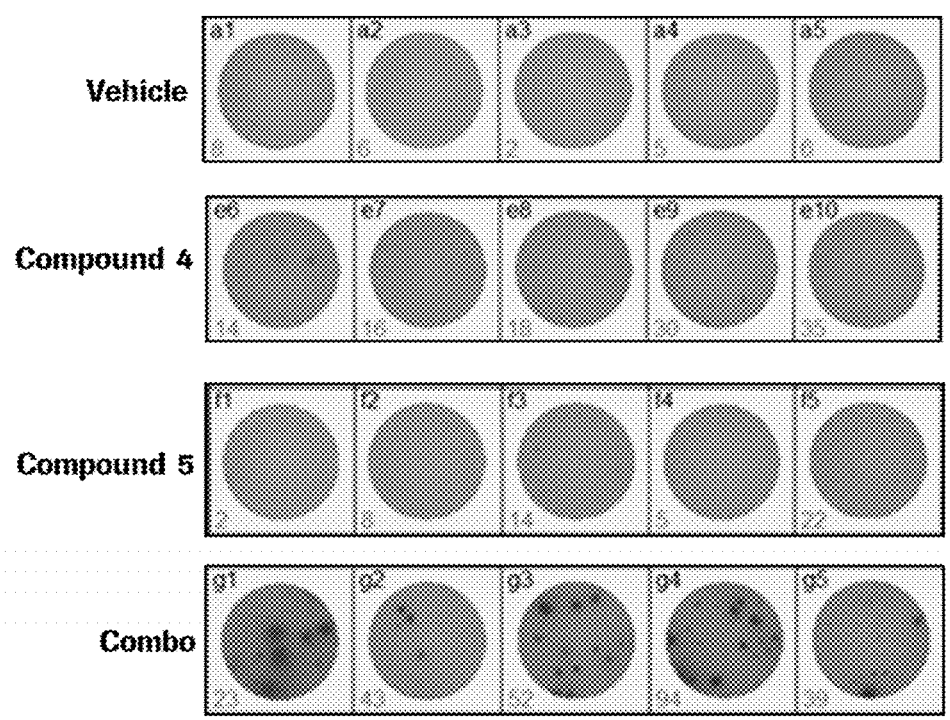
Figure 4-D

SEQUENCE LISTING

<160> NUMBER OF SEQ ID NOS: 3

<210> SEQ ID NO 1
<211> LENGTH: 20
<212> TYPE: DNA
<213> ORGANISM: Hepatitis B virus

<400> SEQUENCE: 1
aagaaaaacc ccgcctgtaa                                                    20

<210> SEQ ID NO 2
<211> LENGTH: 23
<212> TYPE: DNA
<213> ORGANISM: Hepatitis B virus

<400> SEQUENCE: 2
cctgttctga ctactgcctc tcc                                                23

<210> SEQ ID NO 3
<211> LENGTH: 27
<212> TYPE: DNA
<213> ORGANISM: Hepatitis B virus

<400> SEQUENCE: 3
cctgatgtga tgttctccat gttcagc                                            27

COMBINED TREATMENT WITH A TLR7 AGONIST AND AN HBV CAPSID ASSEMBLY INHIBITOR

CROSS REFERENCE TO RELATED APPLICATIONS

This application is a continuation of International Application No. PCT/EP2017/072671, filed Sep. 11, 2017, claiming priority to International Application No. PCT/CN2016/098892, filed Sep. 13, 2016, each of which are incorporated herein by reference in its entirety.

SEQUENCE LISTING

This application contains a Sequence Listing which has been submitted electronically in ASCII format and is hereby incorporated by reference in its entirety. Said ASCII copy, created on Mar. 1, 2019 is named Sequence_Listing.txt and is 789 bytes in size.

The present invention is directed to compositions and methods for treating hepatitis B virus infection. In particular, the present invention is directed to a combination therapy comprising administration of a TLR7 agonist and an HBV capsid assembly inhibitor for use in the treatment of chronic hepatitis B patient.

FIELD OF THE INVENTION

Chronic infection of Hepatitis B virus (HBV) is a serious public health problem worldwide, with more than 240 million people chronically infected worldwide. HBV belongs to the Hepadnaviridae family of viruses. Following entry into hepatocyte, its viral genome is delivered into nucleus where a covalently closed circular DNA (cccDNA) is formed through DNA repair of partially double-stranded viral genomecccDNA serves as the template for transcription of viral RNAs. Viral pre-genomic RNA interacts with other two viral components, capsid protein and polymerase to form capsid particles where viral DNA replication occurs. HBV has an icoshedral core comprising of 240 copies of the capsid (or core) protein. The predominant biological function of capsid protein is to act as a structural protein to encapsidate pre-genomic RNA and form immature capsid particles in the cytoplasm. This step is prerequisite for viral DNA replication. When a near full-length relaxed circular DNA is formed through reverse-transcription of viral pregenomic RNA, an immature capsid becomes a mature capsid. Most copies of the encapsidated genome efficiently associate with cellular lipids and viral envelope proteins (S, M, and L) for virion assembly and secretion. However, non-infectious particles are also produced that greatly outnumber the infectious virions. These empty, enveloped particles are referred to as subviral particles (SVPs). The S, M, and L envelope proteins are expressed from a single ORF (open reading frame) that contains three different start codons. All three proteins share a 226aa sequence, the S-domain, at their C-termini. S-domain contains the HBsAg epitope (Lambert, C. & R. Prange. *Virol J*, 2007, 4, 45).

Many observations showed that several HBV viral proteins could counteract the initial host cellular response by interfering with the viral recognition signaling system and subsequently the interferon (IFN) antiviral activity. Among these, the excessive secretion of HBV empty subviral particles may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* 1993, 150, 4659-4671; Kondo et al. *Journal of Medical Virology* 2004, 74, 425-433; Fisicaro et al. *Gastroenterology*, 2010, 138, 682-93;). Moreover HBsAg has been reported to suppress the function of immune cells such as monocytes, dendritic cells (DCs) and natural killer (NK) cells by direct interaction (Op den Brouw et al. *Immunology*, 2009b, 126, 280-9; Woltman et al. *PLoS One*, 2011, 6, e15324; Shi et al. *J Viral Hepat.* 2012, 19, e26-33; Kondo et al. *ISRN Gasteroenterology*, 2013, Article ID 935295).

HBsAg quantification is a biomarker for prognosis and treatment response in chronic hepatitis B. HBsAg loss and seroconversion is the goal for clinical cure, but is rarely observed in chronically infected patients. Current therapy such as Nucleos(t)ide analogues that inhibit HBV DNA synthesis does not directly affect HBsAg level. Nucleos(t)ide analogs, even with prolonged therapy, have demonstrated very low rates of HBsAg clearance comparable to those observed naturally (Janssen et al. *Lancet*, 2005, 365, 123-9; Marcellin et al. *N. Engl. J. Med.*, 2004, 351, 1206-17; Buster et al. *Hepatology*, 2007, 46, 388-94).

Toll-like receptors (TLRs) detect a wide range of conserved pathogen-associated molecular patterns (PAMPs). They play an important role of sensing invading pathogens and subsequent initiation of innate immune responses. There are 10 known members of the TLR family in human, which are type I transmembrane proteins featuring an extracellular leucine-rich domain and a cytoplasmic tail that contains a conserved Toll/interleukin (IL)-1 receptor (TIR) domain. Within this family, TLR3, TLR7, TLR8, and TLR9 are located within endosomes. TLR7 can be activated by binding to a specific small molecule ligand (i.e., TLR7 agonist) or its native ligand (i.e., single-stranded RNA, ssRNA). Following binding of ssRNA to TLR7, the receptor in its dimerized form is believed to undergo a structural change leading to the subsequent recruitment of adapter proteins at its cytoplasmic domain, including the myeloid differentiation primary response gene 88 (MyD88). Following the initiation of the receptor signalling cascade via the MyD88 pathway, cytoplasmic transcription factors such as interferon regulatory factor 7 (IRF-7) and nuclear factor kappa B (NF-κB) are activated. These transcription factors then translocate to the nucleus and initiate the transcription of various genes, e.g., IFN-α and other antiviral cytokine genes. TLR7 is predominately expressed on plasmacytoid cells, and also on B-cells. Altered responsiveness of immune cells might contribute to the reduced innate immune responses during chronic viral infections. Agonist-induced activation of TLR7 might therefore represent a novel approach for the treatment of chronic viral infections. (D. J Connolly and L. A J O'Neill, Current Opinion in Pharmacology 2012, 12:510-518, P. A. Roethle et al, J. Med. Chem. 2013, 56, 7324-7333).

Treatment with an oral TLR7 agonist represents a promising solution to provide greater efficacy with better tolerability. Pegylated IFN-α (PEG-IFN-α) is currently used to treat chronic HBV and is an alternative to potentially lifelong treatment with antiviral nucleos(t)ide analogues. In a subset of chronic HBV patients, PEG-IFN-α therapy can induce sustained immunologic control of the virus following a finite duration of therapy. However, the percentage of HBV patients that achieve seroconversion with interferon therapy is low (up to 27% for HBeAg-positive patients) and the treatment is typically poorly tolerated. Furthermore, functional cure (defined as HBsAg loss and seroconversion) is also very infrequent with both PEG-IFN-α and nucleos (t)ide treatment. Given these limitations, there is an urgent need for improved therapeutic options to treat and induce a functional cure for chronic HBV. Treatment with an oral, small-molecule TLR7 agonist is a promising approach that has the potential to provide greater efficacy and tolerability (T. Asselah et al, Clin Liver Dis 2007, 11, 839-849).

HBV Capsid Protein Plays Essential Roles in HBV Replication.

Heteroaryldihydropyrimidines or HAP, including compounds named Bay 41-4109, Bay 38-7690 and Bay 39-5493, were discovered in a tissue culture-based screening (Deres K. et al. *Science* 2003, 893). These HAP analogs act as synthetic allosteric activators and are able to induce aberrant capsid formation that leads to degradation of the core protein. HAP analogs also reorganized core protein from preassembled capsids into noncapsid polymers, presumably by interaction of HAP with dimers freed during capsid 'breathing', the transitory breaking of individual intersubunit bonds. Bay 41-4109 was administered to HBV infected transgenic mouse or humanized mouse models and demonstrated in vivo efficacy with HBV DNA reduction (Deres K. et al. *Science* 2003, 893; Brezillon N. et al. *PLoS ONE* 2011, e25096). It was also shown that bis-ANS, a small molecule that acts as a molecular 'wedge' and interferes with normal capsid-protein geometry and capsid formation (Zlotnick A. et al. *J. Virol.* 2002, 4848-4854).

Now, the standard of clinic cure of HBV infection is the loss and/or seroconversion of HBsAg. Even though PEG-IFN-α and nucleos(t)ide are available to HBV patients, the majority (around or more than 90%) of treated patients fail to achieve this goal, which is mainly due to fact that the current therapies cannot elicit the appearance of neutralizing antibodies against HBsAg (anti-HBs), a sign of resolution of HBV infection, in most chronically infected patients. Hence, there is certainly a medical need for treatments with improved success rate of inducing HBsAg loss and/or seroconversion and promoting the production of anti-HBs.

SUMMARY OF THE INVENTION

The present invention relates to a pharmaceutical composition comprising a TLR7 agonist and an HBV capsid assembly inhibitor, in a pharmaceutically acceptable carrier. The "TLR7 agonist" herein is a compound of formula (I) or (II), particularly the "TLR7 agonist" herein is 6-amino-9-[(4-chlorophenyl)methyl]-2-[S(S)-ethylsulfonimidoyl]-N-methyl-8-oxo-N-propyl-purine-7-carboxamide; 6-amino-9-[(4-chlorophenyl)methyl]-2-[S(R)-ethylsulfonimidoyl]-N-methyl-8-oxo-N-propyl-purine-7-carboxamide; 6-amino-9-[(4-chlorophenyl)methyl]-N-ethyl-2[S(S)-ethylsulfonimidoyl]-N-methyl-8-oxo-purine-7-carboxamide; 6-amino-2-[S(R)-ethylsulfonimidoyl]-N-methyl-8-oxo-N-propyl-9-(p-tolylmethyl)purine-7-carboxamide; 6-amino-9-[(4-chlorophenyl) methyl]-2-(S(S)-ethylsulfonimidoyl)-7H-purin-8-one; 6-amino-9-[(4-chlorophenyl)methyl]-2-(S(R)-ethylsulfonimidoyl)-7H-purin-8-one; or 6-amino-2-(S(R)-ethylsulfonimidoyl)-9-(p-tolylmethyl)-7H-purin-8-one; or pharmaceutically acceptable salt, enantiomer or diastereomer thereof. The HBV capsid assembly inhibitor herein is a compound of formula (III) or any one of the compounds disclosed in patent WO2014/037480, WO 2014/184328 and WO2015/132276, particularly the HBV capsid assembly inhibitor herein is 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or pharmaceutically acceptable salt, enantiomer or diastereomer thereof.

BRIEF DESCRIPTION OF THE FIGURES

FIG. 4-D shows the spleens harvested on day 84 in Example 5 to identify anti-HBs antibody-producing B cells by ELISPOT. The spots in the Combo group represented the presence of B cells that actively produced anti-HBs antibodies.

DETAILED DESCRIPTION OF THE INVENTION

Figure 1:
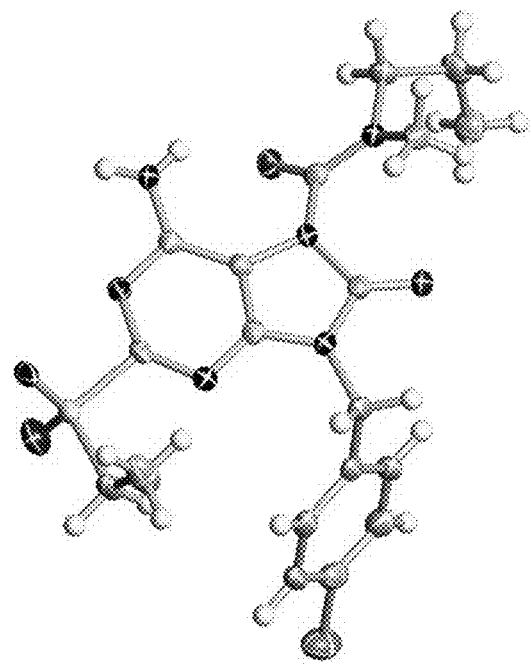
FIG. 1 Single crystal X-ray diffraction of Compound 1.

Unless defined otherwise, all technical and scientific terms used herein have the same meaning as commonly understood by one of ordinary skill in the art to which this invention pertains.

As used herein, the term "$C_{1-6}$alkyl" refers to a monovalent linear or branched saturated hydrocarbon group of 1 to 6 carbon atoms. In particular embodiments, $C_{1-6}$alkyl has 1 to 6 carbon atoms, and in more particular embodiments 1 to 4 carbon atoms. Examples of $C_{1-6}$alkyl include methyl, ethyl, propyl, isopropyl, n-butyl, iso-butyl, sec-butyl or tert-butyl.

As used herein, the term "$C_{1-6}$alkoxy" refers to a group of $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy.

As used herein, the term "halo" or "halogen" are used interchangeably herein and refer to fluoro, chloro, bromo, or iodo.

The term "halo$C_{1-6}$alkyl" refers to an alkyl group wherein at least one of the hydrogen atoms of the alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoroethyl or trifluoromethyl.

The term "carbonyl" alone or in combination refers to the group —C(O)—.

The term "$C_{1-6}$alkylcarbonyl" refers to a group $C_{1-6}$alkyl-C(O)—, wherein the "$C_{1-6}$alkyl" is as defined above. Particular "$C_{1-6}$alkylcarbonyl" group is acetyl.

The term "$C_{1-6}$alkoxycarbonyl" refers to a group $C_{1-6}$alkoxy-C(O)—, wherein the "$C_{1-6}$alkoxy" is as defined above.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclopentyl and cyclohexyl.

The term "—$C_mH_{2m}$—" alone or in combination signifies a saturated, linear or branched chain alkyl group containing m (m≠0) carbon atoms or a bond (m=0). In particular, "—$C_mH_{2m}$—" alone or in combination signifies a saturated, linear or branched chain alkyl group containing 1 to 4 carbon atoms.

The term "carboxy-$C_mH_{2m}$—" refers to a group "—$C_mH_{2m}$—COOH", wherein the "—$C_mH_{2m}$—" is as defined above.

The term "$C_{3-7}$cycloalkyl-$C_mH_{2m}$—" refers to a "$C_{3-7}$cycloalkyl" group as defined above wherein one of the hydrogen atoms of the "$C_{3-7}$cycloalkyl" group is replaced by a "—$C_mH_{2m}$—" group.

The term "heterocyclyl" denotes a monovalent saturated or partly unsaturated mono or bicyclic ring system of 3 to 10 ring atoms, comprising 1 to 5 ring heteroatoms selected from N, O and S, the remaining ring atoms being carbon. In particular embodiments, heterocyclyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, dimethylpyrrolidinyl, ethoxycarbonylpyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, dioxothiomorpholinyl, azepanyl, diazepanyl, homopiperazinyl, or oxazepanyl. Monocyclic saturated heterocyclyl can be further substituted by one to three substituents independently selected from halogen, $C_{1-6}$alkyl and $C_{1-6}$alkoxycarbonyl. Examples for substituted monocyclic saturated heterocyclyl are 4-methylpiperazinyl, dimethylpyrrolidinyl, ethoxycarbonylpyrrolidinyl, difluoropyrrolidinyl, fluoro(methyl)pyrrolidinyl. Examples for bicyclic saturated heterocyclyl are azabicyclo[3.2.1]octyl, quinuclidinyl, oxaazabicyclo[3.2.1]octyl, azabicyclo[3.3.1]nonyl, oxaazabicyclo[3.3.1]nonyl, thiaazabicyclo[3.3.1]nonyl, azaspiro[3.3]heptanyl and oxaazaspiro[3.3]heptanyl. Examples for partly unsaturated heterocyclyl are dihydrofuryl, imidazolinyl, dihydrooxazolyl, tetrahydropyridinyl and dihydropyranyl.

As used herein, the term "diastereomer" refers to a stereoisomer with two or more centers of chirality and whose molecules are not mirror images of one another. Diastereomers have different physical properties, e.g. melting points, boiling points, spectral properties, activities and reactivities.

As used herein, the term "enantiomers" refers to two stereoisomers of a compound which are non-superimposable mirror images of one another.

As used herein, the term "pharmaceutically acceptable salts" refers to salts which are not biologically or otherwise undesirable. Pharmaceutically acceptable salts include both acid and base addition salts.

As used herein, the term "prodrug" refers to a form or derivative of a compound which is metabolized in vivo, e.g., by biological fluids or enzymes by a subject after administration, into a pharmacologically active form of the compound in order to produce the desired pharmacological effect. Prodrugs are described e.g. in the Organic Chemistry of Drug Design and Drug Action by Richard B. Silverman, Academic Press, San Diego, 2004, Chapter 8 Prodrugs and Drug Delivery Systems, pp. 497-558.

The term "pharmaceutically acceptable acid addition salt" refers to those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" refers to those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) which contain one or several chiral centers can either be present as racemates, diastereomeric mixtures, or optically active single isomers.

As used herein, "combo" refers to combination.

As used herein, "RT-PCR" refers to Reverse transcription polymerase chain reaction.

As used herein, "CLIA" refers to chemiluminescence immunoassay.

As used herein, "AAV" refers to adeno-associated virus.

As used herein, "AAV-HBV" refers to a recombinant virus that carries 1.3 copies of the HBV genome packaged in AAV capsids. A chronicle HBV infection mouse model can be established by injecting mice with AAV-HBV through tail vein injection. In this mouse model, active HBV replication results in persist HBV viral markers (e.g., HBV DNA, HBsAg, HBeAg, etc.).

As used herein, "HBsAg" refers to hepatitis B surface antigen.

As used herein, "HBeAg" refers to hepatitis B e antigen.

As used herein, "anti-HBs" refers to antibodies against HBsAg.

As used herein, "HBV specific primers" refers to a pair of single-stranded nucleic acid that serves as starting and ending points for specific amplification of HBV DNA regions.

As used herein, "TLR7" refers to the Toll-like receptor 7 of any species of origin (e.g., human, murine, woodchuck etc.).

As used herein, "TLR7 agonist" refers to a compound that acts as an agonist of TLR7. Unless otherwise indicated, a TLR7 agonist can include the compound in any pharmaceutically acceptable form, including any isomer (e.g., diastereomer or enantiomer), salt, solvate, polymorph, and the like. The TLR agonism for a particular compound may be determined in any suitable manner. For example, assays for detecting TLR agonism of test compounds are described, for example, in U.S. Provisional Patent Application Ser. No. 60/432,650, filed Dec. 11, 2002, and recombinant cell lines suitable for use in such assays are described, for example, in U.S. Provisional Patent Application Ser. No. 60/432,651, filed Dec. 11, 2002.

The present invention relates to a pharmaceutical composition comprising a TLR7 agonist and an HBV capsid assembly inhibitor, in a pharmaceutically acceptable carrier.

In one embodiment of present invention, a "TLR7 agonist" is a compound of formula (I):

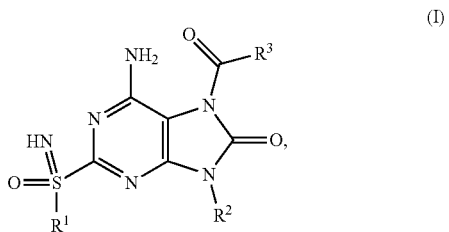

(I)

wherein
$R^1$ is $C_{1-6}$alkyl;
$R^2$ is benzyl, said benzyl being unsubstituted or substituted by one, two or three substituents independently selected from halogen and $C_{1-6}$alkyl;
$R^3$ is —$NR^4R^5$, wherein
  $R^4$ is $C_{1-6}$alkyl or $C_{1-6}$alkoxy$C_{1-6}$alkyl;
  $R^5$ is $(C_{1-6}$alkyl$)_2$NCOOC$_{1-6}$alkyl, $C_{1-6}$alkoxy$C_{1-6}$alkyl, $C_{1-6}$alkoxycarbonyl($C_{1-6}$alkyl)amino$C_{1-6}$alkyl, $C_{1-6}$alkoxycarbonyl(phenyl)$C_{1-6}$alkyl, $C_{1-6}$alkoxycarbonyl$C_{1-6}$alkyl, $C_{1-6}$alkoxycarbonyloxy$C_{1-6}$alkyl, $C_{1-6}$alkyl, $C_{1-6}$alkylcarbonyl($C_{1-6}$alkyl)amino$C_{1-6}$alkyl or pyrrolidinylcarbamoyloxy$C_{1-6}$alkyl; or
  $R^4$ and $R^5$ together with the nitrogen they are attached to form a heterocyclyl;
or pharmaceutically acceptable salt, enantiomer or diastereomer thereof.

In another embodiment of present invention, a "TLR7 agonist" is a compound of formula (II):

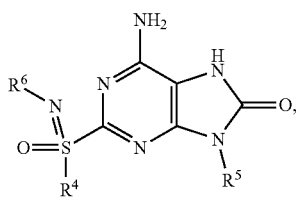

(II)

wherein
$R^4$ is $C_{1-6}$alkyl, halo$C_{1-6}$alkyl, $C_{3-7}$cylcoalkyl$C_{1-6}$alkyl, $C_{1-6}$alkoxy$C_{1-6}$alkyl or pyrrolidinyl$C_{1-6}$alkyl;
$R^5$ is $C_{1-6}$alkyl, phenyl$C_{1-6}$alkyl, pyridinyl$C_{1-6}$alkyl or pyrimidinyl$C_{1-6}$alkyl, said phenyl$C_{1-6}$alkyl, pyridinyl$C_{1-6}$alkyl and pyrimidinyl$C_{1-6}$alkyl are unsubstituted or substituted by one, two or three substituents independently selected from halogen, $C_{1-6}$alkyl, $C_{1-6}$alkoxy, cyano, carboxy, carbamoyl, halo$C_{1-6}$alkyl, $C_{1-6}$alkylsulfonyl, $C_{1-6}$alkoxycarbonyl, $C_{1-6}$alkoxy$C_{1-6}$alkylaminocarbonyl, pyrrolidinylcarbonyl and piperidinylcarbonyl;
$R^6$ is H;
or pharmaceutically acceptable salt, enantiomer or diastereomer thereof.

More particularly, the TLR7 agonist according to present invention relates to 6-amino-9-[(4-chlorophenyl)methyl]-2-[S(S)-ethylsulfonimidoyl]-N-methyl-8-oxo-N-propyl-purine-7-carboxamide; 6-amino-9-[(4-chlorophenyl)methyl]-2-[S(R)-ethylsulfonimidoyl]-N-methyl-8-oxo-N-propyl-purine-7-carboxamide; 6-amino-9-[(4-chlorophenyl)methyl]-N-ethyl-2[S(S)-ethylsulfonimidoyl]-N-methyl-8-oxo-purine-7-carboxamide; 6-amino-2-[S(R)-ethylsulfonimidoyl]-N-methyl-8-oxo-N-propyl-9-(p-tolylmethyl)purine-7-carboxamide; or pharmaceutically acceptable salt, enantiomer or diastereomer thereof. After administration, compounds of formula (I) are metabolized into their active forms which are useful TLR7 agonists.

As used herein, "hepatitis B virus" or "HBV" refers to a member of the Hepadnaviridae family having a small double-stranded DNA genome of approximately 3,200 base pairs and a tropism for liver cells. "HBV" includes hepatitis B virus that infects any of a variety of mammalian (e.g., human, non-human primate, etc.) and avian (duck, etc.) hosts. "HBV" includes any known HBV genotype, e.g., serotype A, B, C, D, E, F, and G; any HBV serotype or HBV subtype; any HBV isolate; HBV variants, e.g., HBeAg-negative variants, drug-resistant HBV variants (e.g., lamivudine-resistant variants; adefovir-resistant mutants; tenofovir-resistant mutants; entecavir-resistant mutants; etc.); and the like.

As used herein, "HBV capsid assembly inhibitor" refers to a compound that inhibits and/or disrupt and/or accelerates and/or hinders and/or delays and or reduces and/or modifies normal HBV capsid assembly (e.g., during maturation) and/or normal capsid disassembly (e.g., during infectivity) and/or perturbs capsid stability, thereby inducing aberrant capsid morphology and function.

In one embodiment of present invention, the HBV capsid assembly inhibitor is a compound of formula (III):

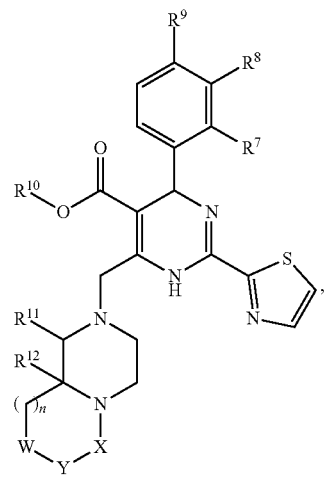

(III)

wherein
$R^7$ is hydrogen, halogen or $C_{1-6}$alkyl;
$R^8$ is hydrogen or halogen;
$R^9$ is hydrogen or halogen;
$R^{10}$ is $C_{1-6}$alkyl;

R[11] is hydrogen, hydroxyC$_{1-6}$alkyl, aminocarbonyl, C$_{1-6}$alkoxycarbonyl or carboxy;
R[12] is hydrogen, C$_{1-6}$alkoxycarbonyl or carboxy-C$_m$H$_{2m}$—;
X is carbonyl or sulfonyl;
Y is —CH$_2$—, —O— or —N(R[13])—,
   wherein R[13] is hydrogen, C$_{1-6}$alkyl, haloC$_{1-6}$alkyl, C$_{3-7}$cycloalkyl-C$_m$H$_{2m}$—, C$_{1-6}$alkoxycarbonyl-C$_m$H$_{2m}$—, —C$_t$H$_{2t}$—COOH, -haloC$_{1-6}$alkyl-COOH, —(C$_{1-6}$alkoxy)C$_{1-6}$alkyl-COOH, —C$_{1-6}$alkyl-O—C$_{1-6}$alkyl-COOH, —C$_{3-7}$cycloalkyl-C$_m$H$_{2m}$—COOH, —C$_m$H$_{2m}$—C$_{3-7}$cycloalkyl-COOH, hydroxy-C$_t$H$_{2t}$—, carboxyspiro[3.3]heptyl or carboxyphenyl-C$_m$H$_{2m}$—, carboxypyridinyl-C$_m$H$_{2m}$—;
W is —CH$_2$—, —C(C$_{1-6}$alkyl)$_2$-, —O— or carbonyl;
n is 0 or 1;
m is 0-7;
t is 1-7;
or pharmaceutically acceptable salts, or enantiomers or diastereomers thereof.

More particularly the HBV capsid assembly inhibitor according to present invention relates to 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or pharmaceutically acceptable salt, enantiomer or diastereomer thereof. In another embodiment, an "HBV capsid assembly inhibitor" is anyone of the compounds disclosed in patent WO2015/132276, WO 2014/184328 and WO2014/037480.

In one embodiment of present invention, the pharmaceutical composition comprises a TLR7 agonist and an HBV capsid assembly inhibitor, wherein TLR7 agonist and HBV capsid assembly inhibitor are independently selected from Table 1. (Compound 5 and 6 were disclosed in patent WO2015/132276).

TABLE 1

| | | List of TLR7 agonist and HBV capsid | |
|---|---|---|---|
| Entry | Class | Compound Name | Structure |
| Compound 1 | TLR7 agonist | 6-Amino-9-[(4-chlorophenyl)methyl]-2-[S(S)-ethylsulfonimidoyl]-N-methyl-8-oxo-N-propyl-purine-7-carboxamide | |
| Compound 2 | TLR7 agonist | 6-Amino-9-[(4-chlorophenyl)methyl]-2-[S(R)-ethylsulfonimidoyl]-N-methyl-8-oxo-N-propyl-purine-7-carboxamide | |
| Compound 3 | TLR7 agonist | 6-Amino-9-[(4-chlorophenyl)methyl]-N-ethyl-2[S(S)-ethylsulfonimidoyl]-N-methyl-8-oxo-purine-7-carboxamide | |

TABLE 1-continued

List of TLR7 agonist and HBV capsid

| Entry | Class | Compound Name | Structure |
|---|---|---|---|
| Compound 4 | TLR7 agonist | 6-Amino-2-[S(R)-ethylsulfonimidoyl]-N-methyl-8-oxo-N-propyl-9-(p-tolylmethyl)purine-7-carboxamide | 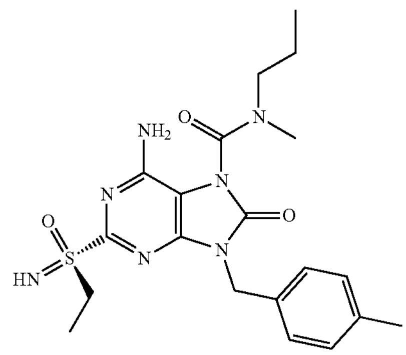 [SMILES: CCCN(C)C(=O)n1c(=O)n(Cc2ccc(C)cc2)c2nc([S@](=N)(=O)CC)nc(N)c21] |
| Compound 5 | HBV capsid inhibitor | 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid | 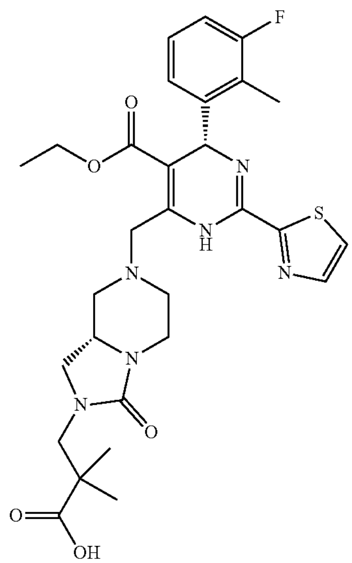 [SMILES: CCOC(=O)C1=C(CN2CCN3C(=O)N(CC(C)(C)C(=O)O)C[C@@H]3C2)NC(c2nccs2)=N[C@H]1c1cccc(F)c1C] |
| Compound 6 | HBV capsid inhibitor | 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid | 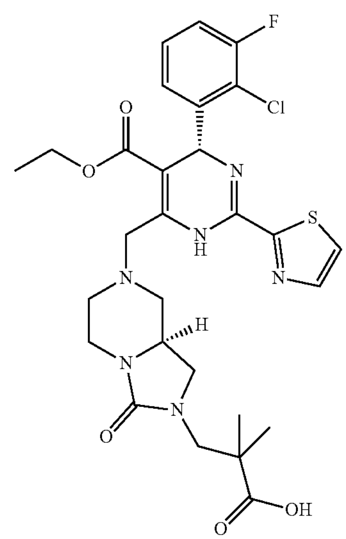 [SMILES: CCOC(=O)C1=C(CN2CCN3C(=O)N(CC(C)(C)C(=O)O)C[C@@H]3C2)NC(c2nccs2)=N[C@H]1c1cccc(F)c1Cl] |

TABLE 1-continued

List of TLR7 agonist and HBV capsid

| Entry | Class | Compound Name | Structure |
|---|---|---|---|
| Compound 1e-A | TLR7 agonist | 6-Amino-9-[(4-chlorophenyl)methyl]-2-(S(S)-ethylsulfonimidoyl)-7H-purin-8-one | 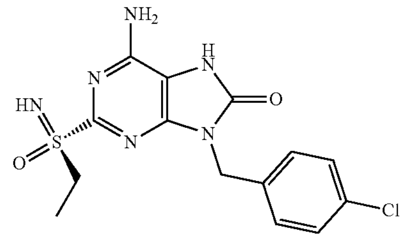 [SMILES: CC[S@](=N)(=O)c1nc(N)c2[nH]c(=O)n(Cc3ccc(Cl)cc3)c2n1] |
| Compound 1e-B | TLR7 agonist | 6-Amino-9-[(4-chlorophenyl)methyl]-2-(S(R)-ethylsulfonimidoyl)-7H-purin-8-one | 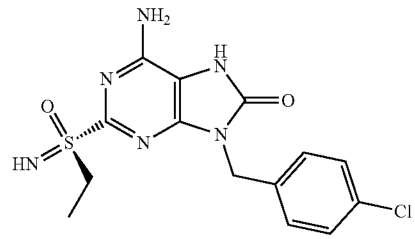 [SMILES: CC[S@@](=N)(=O)c1nc(N)c2[nH]c(=O)n(Cc3ccc(Cl)cc3)c2n1] |
| Compound 4f-A | TLR7 agonist | 6-Amino-2-(S(R)-ethylsulfonimidoyl)-9-(p-tolylmethyl)-7H-purin-8-one | 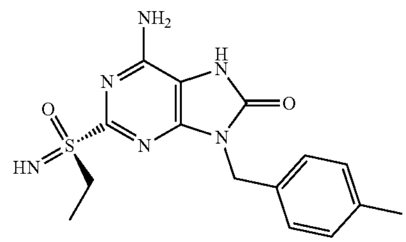 [SMILES: CC[S@@](=N)(=O)c1nc(N)c2[nH]c(=O)n(Cc3ccc(C)cc3)c2n1] |

More particularly, the present invention relates to a pharmaceutical composition comprising a TLR7 agonist and an HBV capsid assembly inhibitor which is selected from any one of the following combinations:

Compound 1 and Compound 5; Compound 1 and Compound 6;
Compound 2 and Compound 5; Compound 2 and Compound 6;
Compound 3 and Compound 5; Compound 3 and Compound 6;
Compound 4 and Compound 5; Compound 4 and Compound 6;
Compound 1e-A and Compound 5; Compound 1e-A and Compound 6;
Compound 1e-B and Compound 5; Compound 1e-B and Compound 6;
Compound 4f-A and Compound 5; and Compound 4f-A and Compound 6.

The Compound 1 to 6, 1e-A, 1e-B and 4f-A of the above said combination can be replaced by its corresponding pharmaceutically acceptable salt, enantiomer or diastereomer, which is another aspect of this invention.

In one embodiment of present invention, the pharmaceutical composition consists of a TLR7 agonist and an HBV capsid assembly inhibitor, in a pharmaceutically acceptable carrier. More particularly, the composition consists of:

6-Amino-9-[(4-chlorophenyl)methyl]-2-[S(S)-ethylsulfonimidoyl]-N-methyl-8-oxo-N-propyl-purine-7-carboxamide and 3-[(8aS)-7-[[(4S)-5-ethoxy carbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-2-[S(S)-ethylsulfonimidoyl]-N-methyl-8-oxo-N-propyl-purine-7-carboxamide and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-2-[S(R)-ethylsulfonimidoyl]-N-methyl-8-oxo-N-propyl-purine-7-carboxamide and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-2-[S(R)-ethylsulfonimidoyl]-N-methyl-8-oxo-N-propyl-purine-7-carboxamide and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-N-ethyl-2[S(S)-ethylsulfonimidoyl]-N-methyl-8-oxo-purine-7-carboxamide and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-N-ethyl-2[S(S)-ethylsulfonimidoyl]-N-methyl-8-oxo-purine-7-carboxamide and 3-[(8aS)-7-[[(4R)-4-(2-chloro-3-fluoro-phenyl)-5-ethoxycarbonyl-2-thiazol-2-yl-1,4-dihydropy-
rimidin-6-yl]methyl]-3-oxo-5,6,8,8a-tetrahydro-1H-
imidazo[1,5-a]pyrazin-2-yl]-2,2-dimethyl-propanoic
acid;

6-Amino-2-[S(R)-ethylsulfonimidoyl]-N-methyl-8-oxo-
N-propyl-9-(p-tolylmethyl)purine-7-carboxamide and
3-[(8aS)-7-[[(4S)-5-ethoxycarbonyl-4-(3-fluoro-2-
methyl-phenyl)-2-thiazol-2-yl-1,4-dihydropyrimidin-
6-yl]methyl]-3-oxo-5,6,8,8a-tetrahydro-1H-imidazo[1,
5-a]pyrazin-2-yl]-2,2-dimethyl-propanoic acid;

6-Amino-2-[S(R)-ethylsulfonimidoyl]-N-methyl-8-oxo-
N-propyl-9-(p-tolylmethyl)purine-7-carboxamide and
3-[(8aS)-7-[[(4R)-4-(2-chloro-3-fluoro-phenyl)-5-
ethoxycarbonyl-2-thiazol-2-yl-1,4-dihydropyrimidin-
6-yl]methyl]-3-oxo-5,6,8,8a-tetrahydro-1H-imidazo[1,
5-a]pyrazin-2-yl]-2,2-dimethyl-propanoic acid;

6-Amino-9-[(4-chlorophenyl)methyl]-2-(S(S)-ethylsulfo-
nimidoyl)-7H-purin-8-one and 3-[(8aS)-7-[[(4S)-5-
ethoxycarbonyl-4-(3-fluoro-2-methyl-phenyl)-2-thi-
azol-2-yl-1,4-dihydropyrimidin-6-yl]methyl]-3-oxo-5,
6,8,8a-tetrahydro-1H-imidazo[1,5-a]pyrazin-2-yl]-2,2-
dimethyl-propanoic acid;

6-Amino-9-[(4-chlorophenyl)methyl]-2-(S(S)-ethylsulfo-
nimidoyl)-7H-purin-8-one and 3-[(8aS)-7-[[(4R)-4-(2-
chloro-3-fluoro-phenyl)-5-ethoxycarbonyl-2-thiazol-2-
yl-1,4-dihydropyrimidin-6-yl]methyl]-3-oxo-5,6,8,8a-
tetrahydro-1H-imidazo[1,5-a]pyrazin-2-yl]-2,2-
dimethyl-propanoic acid;

6-Amino-9-[(4-chlorophenyl)methyl]-2-(S(R)-ethyl-
sulfonimidoyl)-7H-purin-8-one and 3-[(8aS)-7-[[(4S)-
5-ethoxycarbonyl-4-(3-fluoro-2-methyl-phenyl)-2-thi-
azol-2-yl-1,4-dihydropyrimidin-6-yl]methyl]-3-oxo-5,
6,8,8a-tetrahydro-1H-imidazo[1,5-a]pyrazin-2-yl]-2,2-
dimethyl-propanoic acid;

6-Amino-9-[(4-chlorophenyl)methyl]-2-(S(R)-ethyl-
sulfonimidoyl)-7H-purin-8-one and 3-[(8aS)-7-[[(4R)-
4-(2-chloro-3-fluoro-phenyl)-5-ethoxycarbonyl-2-thi-
azol-2-yl-1,4-dihydropyrimidin-6-yl]methyl]-3-oxo-5,
6,8,8a-tetrahydro-1H-imidazo[1,5-a]pyrazin-2-yl]-2,2-
dimethyl-propanoic acid;

6-Amino-2-(S(R)-ethylsulfonimidoyl)-9-(p-tolylmethyl)-
7H-purin-8-one and 3-[(8aS)-7-[[(4S)-5-ethoxycarbo-
nyl-4-(3-fluoro-2-methyl-phenyl)-2-thiazol-2-yl-1,4-
dihydropyrimidin-6-yl]methyl]-3-oxo-5,6,8,8a-
tetrahydro-1H-imidazo[1,5-a]pyrazin-2-yl]-2,2-
dimethyl-propanoic acid; or 6-Amino-2-(S(R)-ethylsulfonimidoyl)-9-(p-tolylmethyl)-
7H-purin-8-one and 3-[(8aS)-7-[[(4R)-4-(2-chloro-3-
fluoro-phenyl)-5-ethoxy carbonyl-2-thiazol-2-yl-1,4-
dihydropyrimidin-6-yl]methyl]-3-oxo-5,6,8,8a-
tetrahydro-1H-imidazo[1,5-a]pyrazin-2-yl]-2,2-
dimethyl-propanoic acid;

in a pharmaceutically acceptable carrier.

Another embodiment of the present invention relates to a pharmaceutical composition consists of 6-Amino-9-[(4-chlorophenyl)methyl]-N-ethyl-2[S(S)-
ethylsulfonimidoyl]-N-methyl-8-oxo-purine-7-carbox-
amide and 3-[(8aS)-7-[[(4S)-5-ethoxycarbonyl-4-(3-
fluoro-2-methyl-phenyl)-2-thiazol-2-yl-1,4-
dihydropyrimidin-6-yl]methyl]-3-oxo-5,6,8,8a-
tetrahydro-1H-imidazo[1,5-a]pyrazin-2-yl]-2,2-
dimethyl-propanoic acid; or 6-Amino-2-[S(R)-ethylsulfonimidoyl]-N-methyl-8-oxo-
N-propyl-9-(p-tolylmethyl)purine-7-carboxamide and
3-[(8aS)-7-[[(4S)-5-ethoxycarbonyl-4-(3-fluoro-2-
methyl-phenyl)-2-thiazol-2-yl-1,4-dihydropyrimidin-
6-yl]methyl]-3-oxo-5,6,8,8a-tetrahydro-1H-imidazo[1,
5-a]pyrazin-2-yl]-2,2-dimethyl-propanoic acid;

in a pharmaceutically acceptable carrier.

In another embodiment of present invention, the pharmaceutical composition can additionally comprise one or more other antiviral agents, which include, but not limited to, lamivudine, adefovir, tenofovir, telbivudine and entecavir.

Typical dosages of a TLR7 agonist and/or an HBV capsid assembly inhibitor can be in the ranges recommended by the manufacturer, and where indicated by in vitro responses in an animal models, can be reduced by up to about one order of magnitude concentration or amount. Thus, the actual dosage will depend upon the judgment of the physician, the condition of the patient, and the effectiveness of the therapeutic method based on the in vitro responsiveness of the appropriate animal models.

Another embodiment of present invention relates to a method for manufacturing a medicament for treatment or prophylaxis of hepatitis B virus infection, characterized in that a TLR7 agonist and an HBV capsid assembly inhibitor are used in the medicament.

A further embodiment of present invention relates to the method for manufacturing a medicament for treatment or prophylaxis of hepatitis B virus infection, characterized in that the TLR7 agonist and the HBV capsid assembly inhibitor are co-administered in the same formulation or different formulation.

For purposes of the present invention, "co-administer" refers to any administration of the TLR7 agonist and the HBV capsid assembly inhibitor as the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. Also, the two active agents can be administered either at the same time, or sequentially.

The TLR7 agonist and the HBV capsid assembly inhibitor can be administered with various pharmaceutically acceptable inert carriers in the form of tablets, capsules, lozengens, troches, hard candies, powders, sprays, creams, salves, suppositories, jellies, gels, pastes, lotions, ointments, elixirs, syrups, and the like. Administration of such dosage forms can be carried out in single or multiple doses. Carries include solid diluents of fillers, sterile aqueous media and various non-toxic organic solvents. Administration of such dosage forms can be carried out through, but not limited to, oral administration, parenteral administration, veterinary administration.

A further embodiment of present invention relates to the method for manufacturing a medicament for treatment or prophylaxis of hepatitis B virus infection, characterized in that the TLR7 agonist and the HBV capsid assembly inhibitor are intended for administration to a subject by the same route or different routes.

A further embodiment of present invention relates to the method for manufacturing a medicament for treatment or prophylaxis of hepatitis B virus infection, characterized in that the TLR7 agonist and the HBV capsid assembly inhibitor are intended for administration to a subject by parenteral or oral administration.

A further embodiment of present invention relates to the method for manufacturing a medicament for treatment or prophylaxis of hepatitis B virus infection, characterized in that the administration of TLR7 agonist and the HBV capsid assembly inhibitor to a subject is simultaneous or sequential. In any of the methods of the present invention, the administration of agents simultaneously can be performed by separately or sequentially administering agents at the same time, or together as a fixed combination. Also, in any of the methods of the present invention, the administration of agents separately or sequentially can be in any order.

Another embodiment of present invention relates to the method for manufacturing a medicament for treatment or prophylaxis of hepatitis B virus infection, characterized in that TLR7 agonist thereof is a compound of formula (I) or formula (II), or pharmaceutically acceptable salt, enantiomer or diastereomer thereof. Particularly, the TLR7 agonist is 6-amino-9-[(4-chlorophenyl)methyl]-2-[S(S)-ethylsulfonimidoyl]-N-methyl-8-oxo-N-propyl-purine-7-carboxamide; 6-amino-9-[(4-chlorophenyl)methyl]-2-[S(R)-ethylsulfonimidoyl]-N-methyl-8-oxo-N-propyl-purine-7-carboxamide; 6-amino-9-[(4-chlorophenyl)methyl]-N-ethyl-2[S(S)-ethylsulfonimidoyl]-N-methyl-8-oxo-purine-7-carboxamide; 6-amino-2-[S(R)-ethylsulfonimidoyl]-N-methyl-8-oxo-N-propyl-9-(p-tolylmethyl)purine-7-carboxamide; 6-amino-9-[(4-chlorophenyl)methyl]-2-(S(S)-ethylsulfonimidoyl)-7H-purin-8-one; 6-amino-9-[(4-chlorophenyl)methyl]-2-(S(R)-ethylsulfonimidoyl)-7H-purin-8-one; or 6-amino-2-(S(R)-ethylsulfonimidoyl)-9-(p-tolylmethyl)-7H-purin-8-one; or pharmaceutically acceptable salt, enantiomer or diastereomer thereof.

Another embodiment of present invention relates to the method for manufacturing a medicament for treatment or prophylaxis of hepatitis B virus infection, characterized in that the HBV capsid assembly inhibitor thereof is a compound of formula (III), or pharmaceutically acceptable salt, enantiomer or diastereomer thereof. Particularly, the HBV capsid assembly inhibitor is 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or pharmaceutically acceptable salt, enantiomer or diastereomer thereof.

Another embodiment of present invention relates to the method for manufacturing a medicament for treatment or prophylaxis of hepatitis B virus infection, characterized in that the medicament additionally comprising one or more other antiviral agents, which include, but not limited to, lamivudine, adefovir, tenofovir, telbivudine and entecavir.

Another embodiment of present invention relates to the method for manufacturing a medicament for treatment or prophylaxis of hepatitis B virus infection, wherein the TLR7 agonist and the HBV capsid assembly inhibitor used in the medicament are:
    6-Amino-9-[(4-chlorophenyl)methyl]-N-ethyl-2[S(S)-ethylsulfonimidoyl]-N-methyl-8-oxo-purine-7-carboxamide and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or
    6-Amino-2-[S(R)-ethylsulfonimidoyl]-N-methyl-8-oxo-N-propyl-9-(p-tolylmethyl)purine-7-carboxamide and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
    in a pharmaceutically acceptable carrier.

Another embodiment of present invention relates to a kit comprising a container comprising a TLR7 agonist and an HBV capsid assembly inhibitor, said kit can further comprise a sterile diluent.

A further embodiment of present invention relates to the said kit, wherein the kit can further comprise a package insert comprising printed instructions directing the use of a combined treatment of a TLR7 agonist and an HBV capsid assembly inhibitor as a method for treatment or prophylaxis of hepatitis B virus infection.

Another embodiment of present invention relates to the said kit, wherein the TLR7 agonist is:
    6-amino-9-[(4-chlorophenyl)methyl]-2-[S(S)-ethylsulfonimidoyl]-N-methyl-8-oxo-N-propyl-purine-7-carboxamide;
    6-amino-9-[(4-chlorophenyl)methyl]-2-[S(R)-ethylsulfonimidoyl]-N-methyl-8-oxo-N-propyl-purine-7-carboxamide;
    6-amino-9-[(4-chlorophenyl)methyl]-N-ethyl-2[S(S)-ethylsulfonimidoyl]-N-methyl-8-oxo-purine-7-carboxamide;
    6-amino-2-[S(R)-ethylsulfonimidoyl]-N-methyl-8-oxo-N-propyl-9-(p-tolylmethyl)purine-7-carboxamide;
    6-amino-9-[(4-chlorophenyl)methyl]-2-(S(S)-ethylsulfonimidoyl)-7H-purin-8-one;
    6-amino-9-[(4-chlorophenyl)methyl]-2-(S(R)-ethylsulfonimidoyl)-7H-purin-8-one; or
    6-amino-2-(S(R)-ethylsulfonimidoyl)-9-(p-tolylmethyl)-7H-purin-8-one;
or pharmaceutically acceptable salt, enantiomer or diastereomer thereof.

Another embodiment of present invention relates to the said kit, wherein the TLR7 agonist and the HBV capsid assembly inhibitor used in the container are:
    6-Amino-9-[(4-chlorophenyl)methyl]-N-ethyl-2[S(S)-ethylsulfonimidoyl]-N-methyl-8-oxo-purine-7-carboxamide and 3-[(8 aS)-7-[[(4S)-5-ethoxy carbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or
    6-Amino-2-[S(R)-ethylsulfonimidoyl]-N-methyl-8-oxo-N-propyl-9-(p-tolylmethyl)purine-7-carboxamide and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
    in a pharmaceutically acceptable carrier.

Another embodiment of present invention relates to a method for the treatment or prophylaxis of hepatitis B virus infection, comprising administration to a subject with an effective first amount of a TLR7 agonist, or pharmaceutically acceptable salt, enantiomer or diastereomer thereof; and a second amount of HBV capsid assembly inhibitor, or pharmaceutically acceptable salt, enantiomer or diastereomer thereof; wherein the TLR7 agonist is 6-amino-9-[(4-chlorophenyl)methyl]-2-[S(S)-ethylsulfonimidoyl]-N-methyl-8-oxo-N-propyl-purine-7-carboxamide; 6-amino-9-[(4-chlorophenyl)methyl]-2-[S(R)-ethylsulfonimidoyl]-N-methyl-8-oxo-N-propyl-purine-7-carboxamide; 6-amino-9-[(4-chlorophenyl)methyl]-N-ethyl-2[S(S)-ethylsulfonimidoyl]-N-methyl-8-oxo-purine-7-carboxamide; 6-amino-2-[S(R)-ethylsulfonimidoyl]-N-methyl-8-oxo-N-propyl-9-(p-tolylmethyl)purine-7-carboxamide; 6-amino-9-[(4-chlorophenyl)methyl]-2-(S(S)-ethylsulfonimidoyl)-7H-purin-8-one; 6-amino-9-[(4-chlorophenyl)methyl]-2-(S(R)-ethylsulfonimidoyl)-7H-purin-8-one; or 6-amino-2-(S(R)-ethylsulfonimidoyl)-9-(p-tolylmethyl)-7H-purin-8-one; or pharmaceutically acceptable salt, enantiomer or diastereomer thereof; and the HBV capsid assembly inhibitor is 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or pharmaceutically acceptable salt, enantiomer or diastereomer thereof.

Another embodiment of present invention relates to use of pharmaceutical composition herein mentioned above as an antiviral medicament, in particular as the medicament for treatment or prophylaxis of hepatitis B virus infection.

Another embodiment of present invention relates to the use of a TLR7 agonist and an HBV capsid assembly inhibitor for the manufacture of pharmaceutical composition herein mentioned above as an antiviral medicament, in particular the medicament for treatment or prophylaxis of hepatitis B virus infection.

EXAMPLES

The invention will be more fully understood by reference to the following examples. They should not, however, be construed as limiting the scope of the invention.

Example 1

6-Amino-9-[(4-chlorophenyl)methyl]-2-[S(S)-ethylsulfonimidoyl]-N-methyl-8-oxo-N-propyl-purine-7-carboxamide (Compound 1) and 6-amino-9-[(4-chlorophenyl)methyl]-2-[S(R)-ethylsulfonimidoyl]-N-methyl-8-oxo-N-propyl-purine-7-carboxamide (Compound 2)

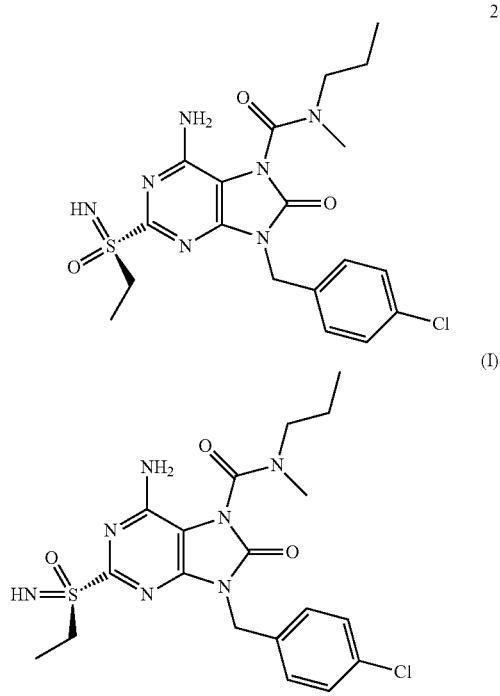

Step 1: Preparation of 4-amino-3-[(4-chlorophenyl)methyl]-2-oxo-1H-imidazole-5-carbonitrile

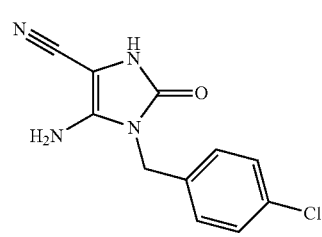

To a solution of triphosgene (5.9 g) in dry THF (40 mL) was added (4-chlorophenyl)methylamine (8.5 g, Accela ChemBio Inc, Catalog number: SY004062-25g) and DIPEA (12.4 g) in dry THF (80 mL) at −80° C. The solution was stirred at −80° C. for 15 mins. A solution of aminomalononitrile p-toluenesulfonate (15.2 g, TCI, Catalog number: A1119-25G) and DIPEA (6.2 g) in dry THF (40 mL) was added at −80° C. After stirred at room temperature for 24 hrs, the reaction was concentrated in vacuo and the residue was partitioned between EtOAc (300 mL) and water (150 mL). The separated organic layer was washed with brine (50 mL) two times, and extracted with sodium hydroxide solution (50 mL, 1 N) two times. The combined sodium hydroxide solution layer was neutralized with 10% wt. sodium hydrogen sulfate solution and extracted with EtOAc (50 mL) two times. The combined organic layer was washed with brine, dried over anhydrous sodium sulfate, filtered and concentrated in vacuo. The residue was triturated with diethyl ether and the resulting precipitate was collected and dried to give 4-amino-3-[(4-chlorophenyl)methyl]-2-oxo-1H-imidazole-5-carbonitrile (8.0 g, Compound 1a) as a yellow solid. MS obsd. (ESI+) [(M+H)+]: 249.

Step 2: Preparation of 6-amino-9-[(4-chlorophenyl)methyl]-2-sulfanyl-7H-purin-8-one

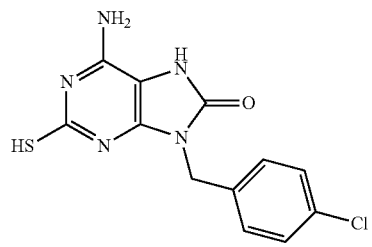

To a solution of 4-amino-3-[(4-chlorophenyl)methyl]-2-oxo-1H-imidazole-5-carbonitrile (8.0 g, 32.0 mmol, Compound 1a) in THF (100 mL) was added benzoylisothiocyanate (11.5 g, 70.4 mmol, TCI, Catalog number: A11596-100G) dropwise. After stirred at room temperature for 12 hrs, the reaction mixture was concentrated in vacuo. The residue was triturated in diethyl ether (100 mL) and the resulting precipitate was collected by filtration.

To a solution of the obtained precipitate in THF (300 mL) was added sodium hydroxide (30 mL, 2 N). The reaction mixture was refluxed for 50 hrs, and then acidified to pH 3 with 10% wt. aqueous sodium hydrogen sulfate solution.

The resulting precipitate was collected by filtration to give a crude product 6-amino-9-[(4-chlorophenyl)methyl]-2-sulfanyl-7H-purin-8-one as a yellow solid (6.4 g, Compound 1b), which was used in the next step without further purification. MS obsd. (ESI+) [(M+H)+]: 308.

Step 3: Preparation of 6-amino-9-[(4-chlorophenyl)methyl]-2-ethylsulfanyl-7H-purin-8-one

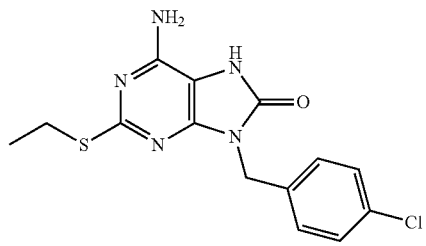

1c

To a solution of 6-amino-9-[(4-chlorophenyl)methyl]-2-sulfanyl-7H-purin-8-one (4.40 g, Compound 1b) in DMF (50 mL) was added potassium carbonate (3.95 g, 28.59 mmol), followed by iodoethane (2.68 g, 17.16 mmol) at 0° C. After stirred at room temperature for 12 hrs, the reaction mixture was poured into water (200 mL), and acidified with 10 wt. % aqueous sodium hydrogen sulfate solution. The resulting precipitate was collected by filtration, and dried to give 6-amino-9-[(4-chlorophenyl)methyl]-2-ethylsulfanyl-7H-purin-8-one (2.50 g, Compound 1c) as a white solid, which was used in the next step without further purification. MS obsd. (ESI+) [(M+H)+]: 336.0

Step 4: Preparation of 6-amino-9-[(4-chlorophenyl)methyl]-2-ethylsulfinyl-7H-purin-8-one

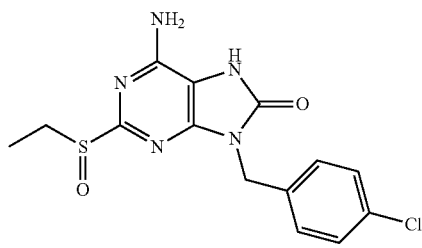

1d

To a suspension of 6-amino-9-[(4-chlorophenyl)methyl]-2-ethylsulfanyl-7H-purin-8-one (2.2 g, Compound 1c) in THF (100 mL) was added m-CPBA (1.36 g, 7.86 mmol) at 0° C. After reaction mixture was stirred at 0° C. for 30 mins, the volume of reaction mixture was reduced in vacuo to about 50 mL. The resulting precipitate was collected by filtration, washed with methanol and dried to give 6-amino-9-[(4-chlorophenyl)methyl]-2-ethylsulfinyl-7H-purin-8-one (1.94 g, Compound 1d) as a white solid. MS obsd. (ESI+) [(M+H)+]: 352.0

Step 5: Preparation of 6-amino-9-[(4-chlorophenyl)methyl]-2-(ethylsulfonimidoyl)-7H-purin-8-one

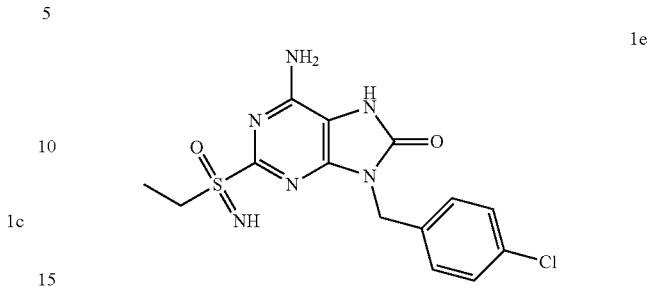

1e

To a solution of 6-amino-9-[(4-chlorophenyl)methyl]-2-ethylsulfinyl-7H-purin-8-one (1.94 g, 5.51 mmol) in Eaton's reagent (30 mL) was added NaN₃ (1.08 g) in portions at 60° C. and the mixture was stirred at this temperature for 30 mins. After cooling, the reaction mixture was poured into a mixture of ice and ammonium hydroxide (100 mL, 1 M). The resulting precipitate was collected by filtration. The residue was purified by prep-HPLC to give 6-amino-9-[(4-chlorophenyl)methyl]-2-(ethylsulfonimidoyl)-7H-purin-8-one (217 mg, Compound 1e) as a white solid. ¹H NMR (400 MHz, DMSO-d₆) δ ppm: 10.61 (s, 1 H), 7.42-7.35 (m, 4 H), 6.98 (s, 2 H), 4.96 (s, 2 H), 4.05 (s, 1 H), 3.42-3.37 (m, 2 H), 1.16 (t, J=7.4 Hz, 3H). MS obsd. (ESI+) [(M+H)+]: 367.0.

Separation of Compound 1e (100 mg) by chiral HPLC afforded Compound 1e-A (faster eluting, 31.8 mg) and Compound 1e-B (slower eluting, 10 mg) as white solid with methanol 5%-40% (0.05% DEA)/CO₂ on ChiralPak IC-3 column.

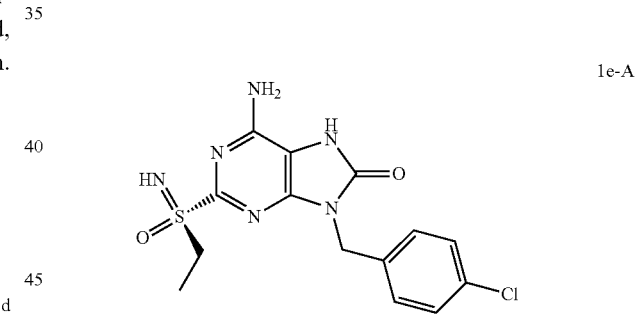

1e-A

6-Amino-9-[(4-chlorophenyl)methyl]-2-[S(S)-(ethylsulfonimidoyl)]-7H-purin-8-one (Compound 1e-A): ¹H NMR (400 MHz, DMSO-d₆) δ ppm: 10.76 (s, 1 H), 7.45-7.33 (m, 4 H), 7.01 (s, 2 H), 4.96 (s, 2 H), 4.03 (s, 1 H), 3.40-3.34 (m, 2 H), 1.17 (t, J=7.4 Hz, 3 H). MS obsd. (ESI+) [(M+H)+]: 367.0.

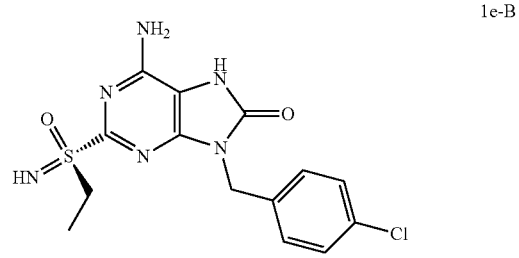 [SMILES: CC[S@@](=N)(=O)c1nc(N)c2[nH]c(=O)n(Cc3ccc(Cl)cc3)c2n1]

1e-B

6-Amino-9-[(4-chlorophenyl)methyl]-2-[S(R)-ethylsulfonimidoyl)]-7H-purin-8-one (Compound 1e-B): ¹H NMR (400 MHz, DMSO-d₆) δ ppm: 10.70 (s, 1 H), 7.46-7.28 (m, 4 H), 7.01 (s, 2 H), 4.96 (s, 2 H), 4.03 (s, 1 H), 3.44-3.36 (m, 2 H), 1.17 (t, J=7.4 Hz, 3 H). MS obsd. (ESI⁺) [(M+H)⁺]: 367.0.

Step 6: Preparation of 6-amino-9-[(4-chlorophenyl)methyl]-2-[S(S)-ethylsulfonimidoyl]-N-methyl-8-oxo-N-propyl-purine-7-carboxamide (Compound 1) and 6-Amino-9-[(4-chlorophenyl)methyl]-2-[S(R)-ethylsulfonimidoyl]-N-methyl-8-oxo-N-propyl-purine-7-carboxamide (Compound 2)

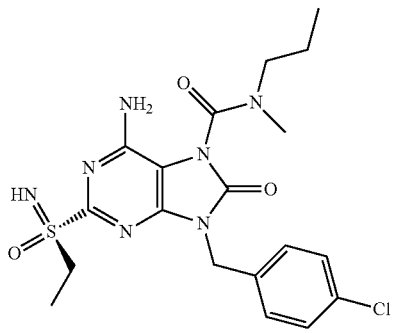

1

To a suspension of 6-amino-9-[(4-chlorophenyl)methyl]-2-[S(S)-(ethylsulfonimidoyl)]-7H-purin-8-one (100 mg, Compound 1e-A) in DIPEA/pyridine (v/v, 1/12, 2.0 mL) was added a solution of N-propyl-N-methyl-carbamoyl chloride (148 mg, 1.09 mmol) dropwise. After stirred at 25° C. for 2 hrs, the reaction mixture was quenched with MeOH (5 mL) and concentrated. The residue was purified by prep-HPLC to give 6-amino-9-[(4-chlorophenyl)methyl]-2-[S(S)-ethylsulfonimidoyl]-N-methyl-8-oxo-N-propyl-purine-7-carboxamide (78.0 mg, compound 1) as a white solid. MS obsd. (ESI⁺) [(M+H)⁺]: 466.2

¹H NMR (DMSO-d₆, 400 MHz) δ ppm: 7.43-7.41 (m, 4 H), 6.90 (s, 2 H), 5.00 (s, 2 H), 4.20 (s, 1 H), 3.46-3.41 (m, 2 H), 3.40-3.39 (m, 2 H), 3.10-3.00 (m, 3 H), 1.69-1.50 (m, 2 H), 1.24-1.12 (m, 3 H), 0.93-0.73 (m, 3 H).

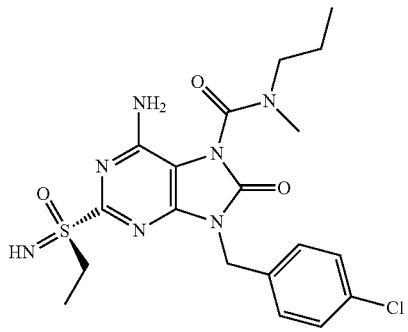

2

To a suspension of 6-amino-9-[(4-chlorophenyl)methyl]-2-[S(R)-(ethylsulfonimidoyl)]-7H-purin-8-one (100 mg, Compound 1e-B) in DIPEA/pyridine (v/v, 1/12, 2.0 mL) was added a solution of N-propyl-N-methyl-carbamoyl chloride (148 mg, 1.09 mmol) dropwise. After stirred at 25° C. for 2 hrs, the reaction mixture was quenched with MeOH (5 mL) and concentrated. The residue was purified by prep-HPLC to give 6-amino-9-[(4-chlorophenyl)methyl]-2-[S(R)-ethylsulfonimidoyl]-N-methyl-8-oxo-N-propyl-purine-7-carboxamide (38.6 mg, compound 2) as a white solid. MS obsd. (ESI⁺) [(M+H)⁺]: 466.1

¹H NMR (DMSO-d₆, 400 MHz) δ ppm: 7.43-7.41 (m, 4 H), 6.90 (s, 2 H), 5.00 (s, 2 H), 4.19 (s, 1 H), 3.46-3.39 (m, 2 H), 3.39-3.38 (m, 2 H), 3.09-2.99 (m, 3 H), 1.69-1.52 (m, 2 H), 1.19 (t, J=7.28 Hz, 3 H), 0.95-0.66 (m, 3 H)

The stereochemistry of compound 1 was determined by single crystal X-ray diffraction shown in FIG. 1.

Example 2

6-Amino-9-[(4-chlorophenyl)methyl]-N-ethyl-2-[S(S)-(ethylsulfonimidoyl)]-N-methyl-8-oxo-purine-7-carboxamide (Compound 3)

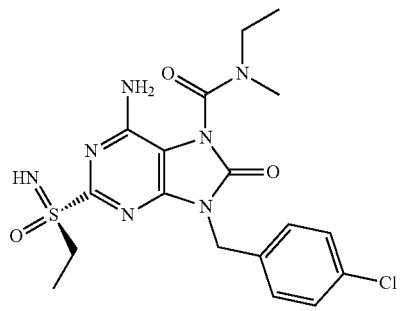

3

To a suspension of 6-amino-9-[(4-chlorophenyl)methyl]-2-[S(S)-(ethylsulfonimidoyl)]-7H-purin-8-one (100 mg, Compound 1e-A) in DIPEA/pyridine (v/v=1/12, 2.0 mL) was added dropwise a solution of N-ethyl-N-methyl-carbamoyl chloride (132 mg, 1.09 mmol). After stirred at 25° C. for 2 hrs, the reaction mixture was quenched with MeOH (5 mL) and concentrated. The residue was purified by prep-HPLC to give 6-amino-9-[(4-chlorophenyl)methyl]-2-[S(S)-ethylsulfonimidoyl]-N-ethyl-8-oxo-N-methyl-purine-7-carboxamide (31.9 mg, compound 3) ¹H NMR (400 MHz, DMSO-d₆) δ ppm: 7.43-7.41 (m, 4 H), 6.90 (s, 2 H), 4.99 (s, 2 H), 4.18 (s, 1 H), 3.48-3.40 (m, 2 H), 3.39 (s, 2 H), 3.05-3.01 (m, 3 H), 1.20-1.14 (m, 6 H). MS obsd. (ESI⁺) [(M+H)⁺]: 452.2.

Figure 2:
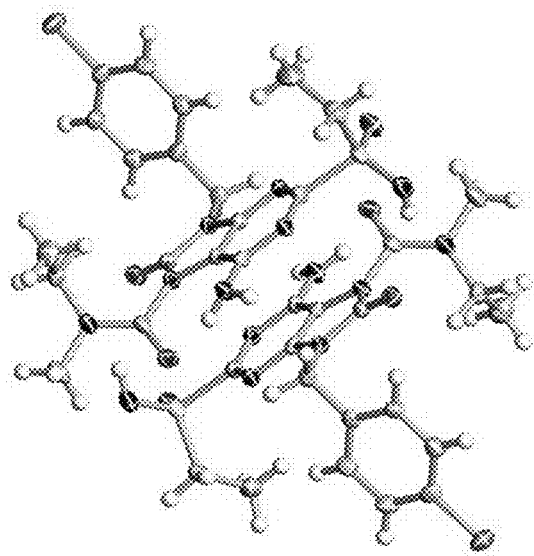
FIG. 2 Single crystal X-ray diffraction of Compound 3.

The stereochemistry of compound 3 was determined by single crystal X-ray diffraction shown in FIG. 2.

Example 3

6-Amino-2-[S(R)-(ethylsulfonimidoyl)]-N-methyl-8-oxo-N-propyl-9-(p-tolylmethyl)purine-7-carboxamide (Compound 4)

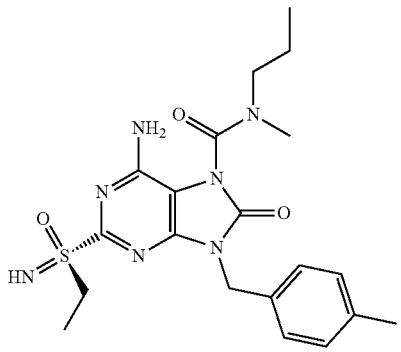

4

Step 1: Preparation of 1-(isocyanatomethyl)-4-methylbenzene

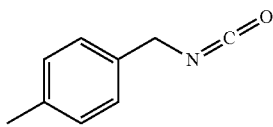

4a

To a solution of triphosgene (40.5 g, 136.3 mmol) in anhydrous DCM (1.2 L) was added dropwise a solution of p-tolylmethanamine (50.0 g, 413.2 mmol) and $Et_3N$ (83.4 g, 826.4 mmol) in DCM (800 mL) at −78° C. under nitrogen. After stirred for 1 h, reaction mixture was allowed to rise to 20° C. and stirred for another 12 hrs. The mixture was diluted with DCM (2.0 L), and the solids were removed by filtration. The filtrate was concentrated in vacuo. The residue was purified by distillation (b.p. 150° C., 10 mmHg) to give 1-(isocyanatomethyl)-4-methylbenzene (30.0 g, Compound 4a) as colorless oil.

Step 2: Preparation of 5-amino-1-(4-methylbenzyl)-2-oxo-2,3-dihydro-1H-imidazole-4-carbonitrile

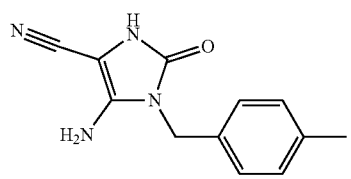

4b

To a solution of aminomalononitrile 4-methylbenzenesulfonate (32.7 g, 129.5 mmol) in dry THF (800 mL) was added 1-(isocyanatomethyl)-4-methylbenzene (20.0 g, Compound 4a) and DIPEA (12.2 g, 94.2 mmol) at room temperature. After stirred at 20° C. for 16 hrs, the reaction was concentrated in vacuo and the residue was poured into water (500 mL) and the resulting grey solid was collected by filtration. The filtrate was extracted with EtOAc (300 mL) three times. The separated organic layer was dried over sodium sulfate, filtered and concentrated. The residue was combined with the grey solid. To the combined solid was added THF (200 mL) and aqueous sodium hydroxide solution (300 mL, 1N). The mixture was stirred 50° C. for 1 h, cooled to room temperature, neutralized with 15% sodium hydrogen sulfate and extracted with EtOAc (500 mL) three times, the separated organic layer were washed with brine, dried over sodium sulfate, filtered and concentrated in vacuo to give 5-amino-1-(4-methylbenzyl)-2-oxo-2,3-dihydro-1H-imidazole-4-carbonitrile (26.6 g, Compound 4b) as grey solid which was used in next step without further purification. MS obsd. ($ESI^+$) [$(M+H)^+$]: 229.2.

Step 3: Preparation of 6-amino-9-(p-tolylmethyl)-2-sulfanyl-7H-purin-8-one

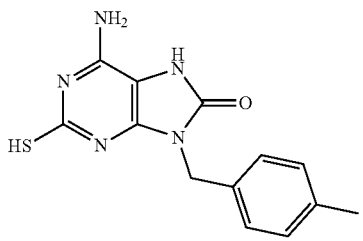

4c

To a solution of 5-amino-1-(4-methylbenzyl)-2-oxo-2,3-dihydro-1H-imidazole-4-carbonitrile (27.0 g, Compound 4b) in THF (500 mL) was added benzoyl isothiocyanate (48.3 g) dropwise. After stirred at 20° C. for 16 hrs, the reaction mixture was concentrated in vacuo. The residue was triturated with THF (200 mL) and the resulting precipitate was collected by filtration.

To a solution of the obtained precipitate in THF (200 mL) was added aqueous sodium hydroxide (70 mL, 2N). The mixture was refluxed at 80° C. for 20 hrs, and then acidified to pH 5 with 15% aq potassium hydrogen sulfate and the resulting precipitate was collected by filtration to give 6-amino-9-(p-tolylmethyl)-2-sulfanyl-7H-purin-8-one (20.0 g, Compound 4c) as yellow solid. The product was used for the next step without further purification. MS obsd. ($ESI^+$) [$(M+H)^+$]: 288.

Step 4: Preparation of 6-amino-2-ethylsulfanyl-9-(p-tolylmethyl)-7H-purin-8-one

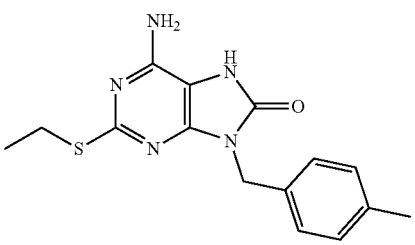

4d

To a solution of 6-amino-9-(p-tolylmethyl)-2-sulfanyl-7H-purin-8-one (19.0 g, Compound 4c) in DMF (150 mL) was added potassium carbonate (13.7 g, 99.3 mmol), followed by iodoethane (7.2 g, 46.3 mmol). After stirred at 25° C. for 16 hrs, the mixture was poured into water (800 mL), The resulting precipitate was separated out and dried to give the crude product of 6-amino-2-ethylsulfanyl-9-(p-tolylmethyl)-7H-purin-8-one (13.0 g, Compound 4d) as a yellow solid. MS obsd. (ESI$^+$) [(M+H)$^+$]: 316.1.

Step 5: Preparation of 6-amino-2-ethylsulfinyl-9-(p-tolylmethyl)-7H-purin-8-one

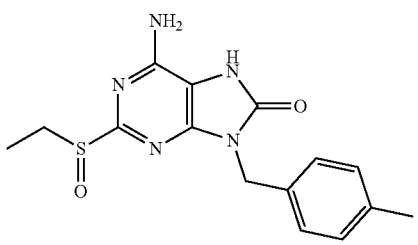

4e

To a solution of 6-amino-2-ethylsulfanyl-9-(p-tolylmethyl)-7H-purin-8-one (8.8 g, Compound 4d) in DMF (100 mL) was added m-CPBA (8.7 g, 50.0 mmol) in DMF (20.0 mL) dropwise at 0° C. After stirred at this temperature for 2 h, the reaction mixture was poured into water (400 mL). The resulting yellow precipitate was filtered, washed with MTBE (50 mL) and dried to give 6-amino-2-ethylsulfinyl-9-(p-tolylmethyl)-7H-purin-8-one (3.5 g, Compound 4e) as yellow solid. MS obsd. (ESI$^+$) [(M+H)$^+$]: 332.2.

Step 6: Preparation of 6-amino-2-(ethylsulfonimidoyl)-9-(p-tolylmethyl)-7H-purin-8-one

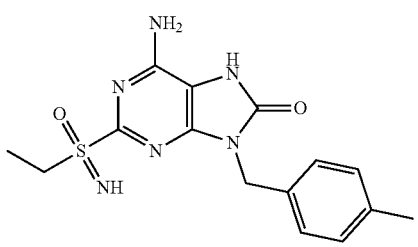

4f

To a solution of 6-amino-2-ethylsulfinyl-9-(p-tolylmethyl)-7H-purin-8-one (4.3 g, Compound 4e) in Eaton's regent (30.0 mL) was added NaN$_3$ (2.1 g, 32.0 mmol) in portions at 55° C. After stirred at 55° C. for 30 min, the reaction mixture was poured into 2 M ammonium hydroxide solution (200 mL) at 0° C., the resulting yellow precipitate was filtered. The crude product was purified by pre-HPLC to give 6-amino-2-(ethylsulfonimidoyl)-9-(p-tolylmethyl)-7H-purin-8-one (2.0 g, Compound 4f) as a white solid.
$^1$H NMR (400 MHz, DMSO-d$_6$) δ ppm: 10.53 (s, 1 H), 7.24 (d, J=8.03 Hz, 2 H), 7.13 (d, J=8.03 Hz, 2 H), 6.94 (br. s., 2 H), 4.91 (s, 2 H), 4.03 (s, 1 H), 3.36-3.41 (m, 2 H), 2.26 (s, 3 H), 1.18 (t, J=7.28 Hz, 3 H). MS obsd. (ESI$^+$) [(M+H)$^+$]: 347.

Separation of Compound 4f by chiral HPLC afforded Compound 4f-A (faster eluting, 56.8 mg) and Compound 4f-B (slower eluting, 56.7 mg) as white solids with methanol 5%-40% (0.05% DEA)/CO$_2$ on ChiralPak AD-3 column.

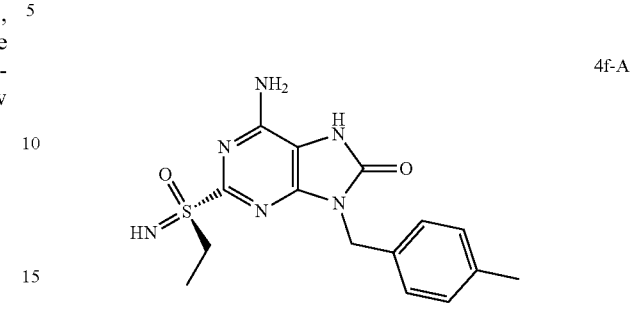

4f-A

Compound 4f-A: $^1$H NMR (400 MHz, DMSO-d$_6$) δ ppm: 10.52 (br. s., 1 H), 7.23 (d, J=8.0 Hz, 2 H), 7.13 (d, J=7.9 Hz, 2 H), 6.94 (br. s., 2 H), 4.90 (s, 2 H), 4.03 (s, 1 H), 3.42-3.33 (m, 2 H), 2.25 (s, 3 H), 1.17 (t, J=7.3 Hz, 3 H). MS obsd. (ESI$^+$) [(M+H)$^+$]: 347.

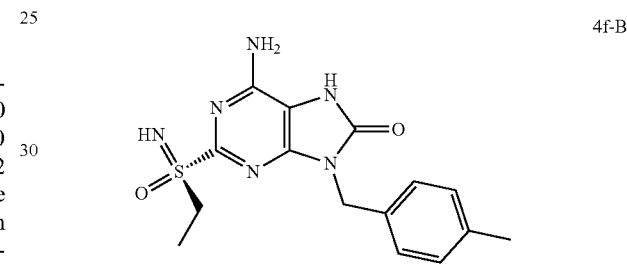

4f-B

Compound 4f-B: $^1$H NMR (400 MHz, DMSO-d$_6$) δ ppm: 10.56 (br. s., 1 H), 7.23 (d, J=8.0 Hz, 2 H), 7.13 (d, J=8.0 Hz, 2 H), 6.95 (br. s., 2 H), 4.90 (s, 2 H) 4.03 (s, 1 H), 3.44-3.29 (m, 2 H), 2.25 (s, 3 H), 1.17 (t, J=7.3 Hz, 3 H). MS obsd. (ESI$^+$) [(M+H)$^+$]: 347.

Step 6: Preparation of 6-amino-2-[S(R)-ethylsulfonimidoyl]-N-methyl-8-oxo-N-propyl-9-(p-tolylmethyl)purine-7-carboxamide

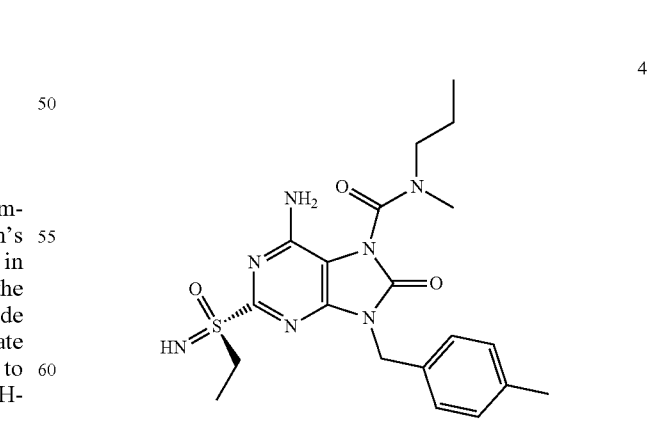

4

To a suspension of (R)-6-amino-2-(ethylsulfonimidoyl)-9-(p-tolylmethyl)-7H-purin-8-one (200.0 mg, Compound 4f-A) in DIPEA/Py (v/v=1/1, 3.0 mL) was added N-methyl-N-propyl-carbamoyl chloride (308 mg, 2.28 mmol) dropwise. After stirred at 25° C. for 2 hrs, the reaction mixture was diluted with water, extracted with EtOAc (10 mL) three times. The combined organic layers was dried with sodium sulfate, filtered and concentrated. The residue was purified by prep-HPLC to give 6-amino-2-[S(R)-(ethylsulfonimidoyl)]-9-(4-methylbenzyl)-9H-purin-8-yl methyl (propyl) carbamate (58.1 mg, compound 4) as a white solid. $^1$H NMR (400 MHz, DMSO-d$_6$) δ ppm: 7.28 (d, J=7.8 Hz, 2 H), 7.15 (d, J=7.8 Hz, 2 H), 6.88 (br. s., 2 H), 5.03-4.87 (m, 2 H), 4.19 (s, 1 H), 3.61-3.36 (m, 4 H), 3.11-2.96 (m, 3 H), 2.26 (s, 3 H), 1.72-1.45 (m, 2 H), 1.20 (t, J=7.2 Hz, 3 H), 0.97-0.65 (m, 3 H). MS obsd. (ESI$^+$) [(M+H)$^+$]: 446.

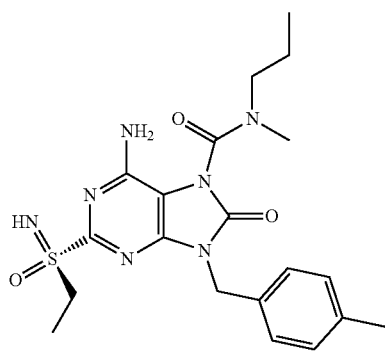

4-a

Compound 4-a was prepared in analogy to compound 4, step 6 by using 6-amino-2-(ethylsulfonimidoyl)-9-(p-tolylmethyl)-7H-purin-8-one (Compound 4f-B) instead of ((R)-6-amino-2-(ethylsulfonimidoyl)-9-(p-tolylmethyl)-7H-purin-8-one (Compound 4f-A). 6-Amino-2-[S(S)-ethylsulfonimidoyl]-N-methyl-8-oxo-N-propyl-9-(p-tolylmethyl)purine-7-carboxamide (Compound 4-a, 40.1 mg) was obtained as a white solid: $^1$H NMR (400 MHz, DMSO-d$_6$) δ ppm: 7.28 (d, J=7.5 Hz, 2 H), 7.15 (d, J=7.5 Hz, 2 H), 6.89 (br. s., 2 H), 5.03-4.86 (m, 2 H), 4.19 (s, 1 H), 3.49-3.37 (m, 4 H), 3.08-3.00 (m, 3 H), 2.27 (s, 3 H), 1.70-1.48 (m, 2 H), 1.20 (t, J=7.2 Hz, 3 H), 0.95-0.71 (m, 3 H). MS obsd. (ESI$^+$) [(M+H)$^+$]: 446.3.

Figure 3:
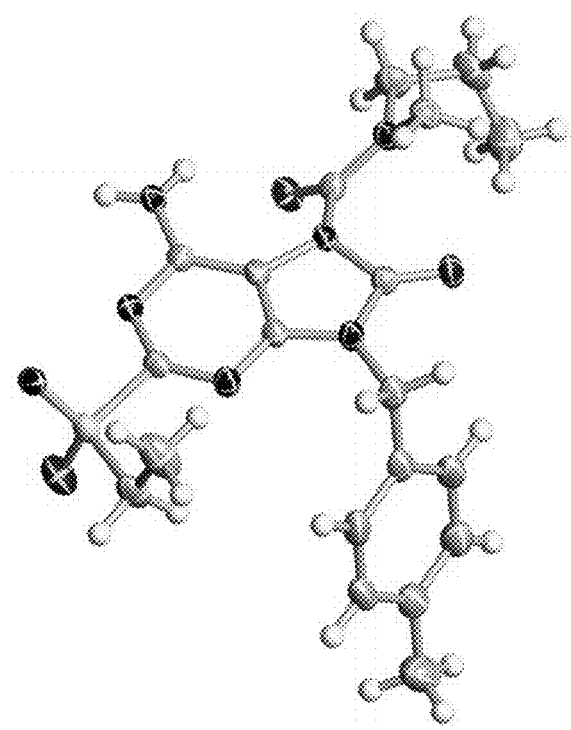
FIG. 3 Single crystal X-ray diffraction of Compound 4-a.

The stereochemistry of compound 4-a was determined by single crystal X-ray diffraction shown in FIG. 3.

Example 4

HEK293-Blue-hTLR-7 Cells Assay:

A stable HEK293-Blue-hTLR-7 cell line was purchased from InvivoGen (Cat.#: hkb-htlr7, San Diego, Calif., USA). These cells were designed for studying the stimulation of human TLR7 by monitoring the activation of NF-κB. A reporter gene of secreted embryonic alkaline phosphatase (SEAP) was placed under the control of the IFN-β☐minimal promoter fused to five NF-κB and AP-1-binding sites. SEAP was induced by the activation of NF-κB and AP-1 upon stimulating HEK-Blue hTLR7 cells with TLR7 ligands. SEAP activity in cell culture supernatant was determined using QUANTI-Blue™ kit (Cat.#: rep-qb1, Invivogen, San Diego, Calif., USA) at a wavelength of 640 nm. Such reporter assays have been widely used for evaluation of TLR7 agonism (Tsuneyasu Kaisho and Takashi Tanaka, Trends in Immunology, Volume 29, Issue 7, July 2008, Pages 329.sci; Hiroaki Hemmi et al, Nature Immunology 3, 196-200 (2002).

Specifically, HEK293-Blue-hTLR7 cells were incubated at a density of 250,000~450,000 cells/mL in a volume of 180 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum for 24 h. The cells were then incubated with 20 μL of test compound in a serial dilution at 37° C. in a CO$_2$ incubator for 20 hours. Then 20 μL of the supernatant from each well was incubated with 180 μL Quanti-blue substrate solution at 37° C. for 2 hours and the absorbance was measured at 620~655 nm using a spectrophotometer. Compound 4 and Compound 3 are efficiently converted into the active moieties, Compound 4f-A and Compound 1e-A respectively. As shown in Table 1, the potency of Compound 4f-A and Compound 1e-A to active TLR7 in HEK293-hTLR7 assay was 0.11 μM and 0.071 μM, respectively. Compound 1 and Compound 2 are efficiently converted into the active moieties, Compound 1e-A and Compound 1e-B, respectively, and the potency of Compound 1e-A and Compound 1e-B to active TLR7 in HEK293-hTLR-7 assay was 0.071 μM and 0.085 μM, respectively. Since the active moiety of the ASIP compounds required less than micromolar concentrations to activate hTLR7 in vitro, such exceptionally high potency allowed the evaluation and led to unexpected finding of the in vivo antiviral efficacy of weekly or bi-weekly administration of these compounds alone or in combination with a capsid inhibitor.

TABLE 1

Activity of Compounds (active form and prodrugs) in HEK293-hTLR-7 assay

| Prodrug | HEK293-hTLR-7 EC$_{50}$ (Prodrug, μM) | Corresponding Active Form | HEK293-hTLR-7 EC$_{50}$ (Active form, μM) |
| --- | --- | --- | --- |
| Compound 1 | 32.1 | Compound 1e-A | 0.071 |
| Compound 2 | 44.1 | Compound 1e-B | 0.085 |
| Compound 3 | 40.5 | Compound 1e-A | 0.071 |
| Compound 4 | 110 | Compound 4f-A | 0.11 |

Example 5

A Combination of TLR7 Agonist (Compound 4) and HBV Capsid Assembly Inhibitor (Compound 5) Potently Reduced HBV DNA and HBsAg in AAV-HBV Mouse Model Animal Model 4-week old male C57BL/6 mice, specific pathogen free, were purchased from Shanghai Laboratory Animal Center of Chinese Academy of Sciences (SLAC) and housed in an animal care facility in individually ventilated cages under controlled temperature and light conditions following the Institutional Animal Care guidelines. AAV-HBV virus was purchased from Beijing FivePlus Molecular Medicine Institute (Beijing, China). This recombinant virus carries 1.3 copies of the HBV genome, which was packaged in AAV serotype 8 (AAV8) capsids. C57BL/6 mice were injected with 200 μL of recombinant virus, diluted in saline buffer, through tail vein injection. After 3-4 weeks, animals were bled to monitor HBV genomic DNA and surface antigen (HBsAg) in serum, and then were randomly grouped according to these HBV biomarkers.

Measurement of HBV Biomarkers

Serum HBsAg was measured using CLIA kits (Autobio Diagnostics Co., Ltd, Zhengzhou, China) according to the manufacturer's instructions. The lower limit of detection (LLOQ) for HBsAg was 0.05 IU/mL. 500-fold dilution of serum was used to obtain values within the linear range of standard curves. Serum HBV DNA was extracted using a MagNA Pure 96 DNA and Viral NA Small Volume Kit (Roche) following the manufacturer's instructions. The DNA samples were analyzed by real-time quantitative PCR (qPCR) using a HBV-specific primer and probe set for specific amplification and detection of a 128 bp HBV genome region from the nucleotide 2969 to 3096. The sequences of the primers and probe are shown as follows:

```
Forward primer:
                                        (SEQ ID 1)
AAGAAAAACCCCGCCTGTAA;

Reverse primer:
                                        (SEQ ID 2)
CCTGTTCTGACTACTGCCTCTCC;

HBV-Probe:
                                        (SEQ ID 3)
5'TAMRA-CCTGATGTGATGTTCTCCATGTTCAGC-BHQ2-3'.
```

Anti-HBs antibody was examined in mouse serum using the anti-HBs CLIA kit (Antobio, Zhengzhou, China) according to the manufacturer's instruction with modification. ~15 µL of the diluted (1:3) mouse serum samples were thawed at room temperature for 10 mins. 6 µL of sample was further diluted in 30 µL of PBS to make the final dilution 1:18 for the antibody test. Standard curve were prepared with monoclonal mouse antibody Anti-Hepatitis B Virus Surface Antigen (Ad/Ay) antibody [S35] (Abcam ab20402) in diluted Naive mouse serum (1:18 dilution in PBS). 1 µL of 1 mg/ml anti-HBs antibody was added into 500 µL of diluted mouse serum to make standard 1 as final concentration 2000 ng/ml. 50 µL of standard 1 then was added into 150 µL of diluted mouse serum to make standard 2 (1:4 dilution). 7 points standards were required for the test. The final concentration of standard 7 was (0.488 ng/ml). Blank serum was used as background control. 25 µL of diluted serum sample/standards/Blank was transferred into 96-well plate. Samples were incubated at room temperature for 1 hour followed by 3 times washing with 300 µL of PBST. 0.5 mg/ml of Goat anti-mouse IgG Biotinylated (Mabtech 3825-6-250) was diluted into PBS to final concentration 1 µg/ml (1:500 dilution). 500 of diluted anti-mouse IgG Bio was added into plate, incubated at room temperature for 1 hour followed by 3 times washing with 300 µL of PBST. Streptavidin-HRP (Mabtech 3310-9) was diluted into PBS (1:250). 50 µL of diluted Streptavidin-HRP was incubated at room temperature for 1 hour followed by 3 times washing with 300 µL of PBST. Substrate A and substrate B (AntuBio) were mixed. 50 µL of mixture were added into plated and incubated for 10 mins before subjected to luminescence reading with Envision microplate reader. The lower limit of detection for anti HBsAb was 36 ng/mL. The anti HBsAb results were calculated from Luminescence raw data fitting on the anti HBsAb standard curve by SoftMax Pro (v5.4.1) software.

An ELISPOT assay to detect anti-HBs-secreting B cells was performed with spleenocytes using a Mouse IgG ELIS-Pot Basic (HRP) kit (Mabtech 3825-2H).HBsAg (AYW) 50 ug (1 mg/ml) (Abcam Ab7374) was diluted 100 times into 10 µg/ml in PBS. PVDF plate (Millipore type MSIP) was treated with 15 µL of 35% ethanol/well for maximum 1 min followed by 5 times washing with 200 µL of ddH2O. 100 µL of diluted HBsAg was added into the wells and incubated overnight at 4-8° C. Plate was washed with 200 µL sterile PBS to remove excess antibody. 200 µL of RPMI1640 containing 10% FBS were added and incubate 2 hours at 37° C. to block to plate. Fresh Spleen in PBS was transferred into the gentle MACS C Tubes (Milterny 130-096-334) containing 5 ml 2% RPMI1640. Sample was then subjected to gentleMacs Dissociator at Program m_spleen_03_02. The dissociated mixture was then filtered through on 70 µM cell strainer. 15 ml of 2% RPMI1640 was used to wash the cell strainer. Cells were centrifuged at 300×g for 5 mins at room temperature. 1 ml of ACK lysis buffer was added and incubated at room temperature for 5 mins to lyse red blood cells. 15 ml of 2% RPMI1640 was added to wash the cells. Cells were centrifuged at 300×g for 5 mins at room temperature and then re-suspended in 5 ml of complete RPMI1640, followed by filtered through on 70 µM cell strainer. Cells were countered by BioRad cell counter. $2 \times 10^6$ cells/200 µL were added into the wells and incubated at 37° C. for overnight. Cells were removed in the plate followed by washing 5 times with 200 µL of PBS. 0.5 mg/ml of Goat anti-mouse IgG Biotinylated (Mabtech 3825-6-250) was diluted into PBS containing 0.5% FBS to final concentration 1 µg/ml (1:500 dilution). 100 µl of diluted anti-mouse IgG Bio was added into plate, incubated at room temperature for 2 hour followed by 5 times washing with 200 µL of PBS. Streptavidin-HRP (Mabtech 3310-9) was diluted into PBS containing 0.5% FBS (1:200). 100 µL of diluted Streptavidin-HRP was incubated at room temperature for 1 hour followed by 5 times washing with 300 µL of PBS. 100 µL of AEC substrate solution (BD 551951) was added into the wells and develop until distinct spots emerge (less than 10 mins). Color development was stopped by extensively washing with ddH2O. The plate was left to dry and spots was pictured and counted with microscope AID ELISPOT.

Experiment Design and Results

As shown in Table 2, a total of 20 mice were stratified into 4 groups for the study. In Group 01, animals were treated with Vehicle every other day (QOD) for 42 days and served as the placebo control. In Group 02, Compound 4 was dosed once weekly (QW) at 10 mg/kg for 42 days. Compound 5 was dosed once daily (QD) at 20 mg/kg for 42 days alone in Group 03, or in combination with 10 mg/kg of Compound 4 QW in Group 04. All the test articles were administered by oral gavage (PO) with a total dose volume of 10 mL/kg. The 42-day treatment was followed by a 42-day off-treatment period. Animals were submandibularly bled once weekly for serum collection until the study end. The serum samples were subjected to the analysis of HBV biomarkers. Upon study termination on day 84, mouse spleens were also collected for ELISPOT assay to detect B cells producing anti-HBs antibodies.

TABLE 2

Combination study design in AAV-HBV mouse model for Compound 4 and 5

| Tx Grp | Treatment | Dose (mg/kg) | Dose Vol (mL/kg) | Dose Route | Dose Schedule | No. An |
|---|---|---|---|---|---|---|
| 01 | Vehicle | 0 | 10 | p.o. | QOD Days 0~41 | 5 |
| 02 | Compound 4 | 10 | 10 | p.o. | QW Days 0~41 | 5 |
| 03 | Compound 5 | 20 | 10 | p.o. | QD Days 0~41 | 5 |

TABLE 2-continued

Combination study design in AAV-HBV mouse model for Compound 4 and 5

| Tx Grp | Treatment | Dose (mg/kg) | Dose Vol (mL/kg) | Dose Route | Dose Schedule | No. An |
|---|---|---|---|---|---|---|
| 04 | Compound 4 and Compound 5 | 10 and 20 | 5 and 5 | p.o. and p.o. | QW and QD Days 0~41 | 5 |

Figure 4:
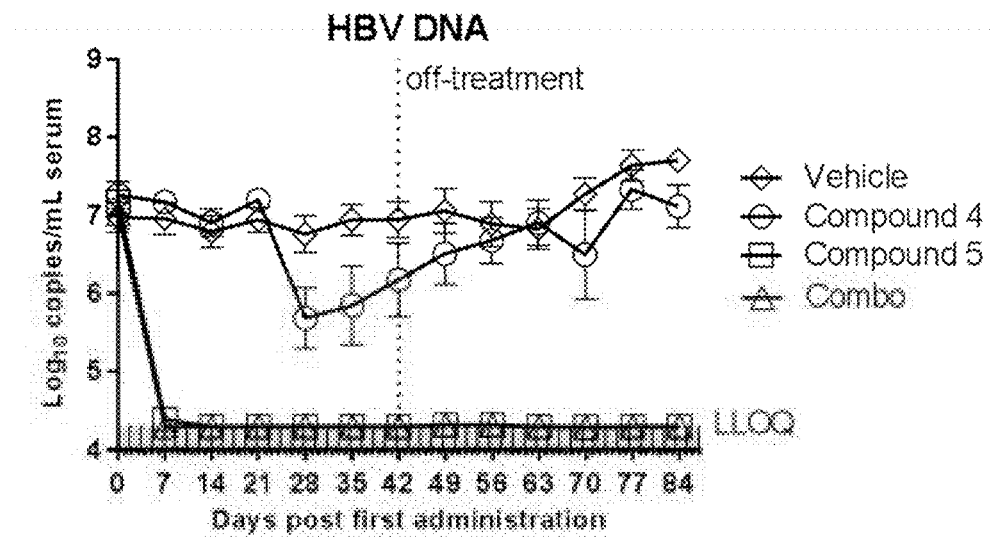
FIG. 4 shows the HBV DNA (FIG. 4A), HBsAg (FIG. 4B), and anti-HBs antibody level (FIG. 4C) of the AAV-HBV infected mice treated with Vehicle, 10 mg/kg of Compound 4 once weekly, 20 mg/kg of Compound 5 once daily, and combination therapy for 42 days followed by a 42-day off-treatment period. The results are presented as mean±SEM. LLOQ: lower limit of quantification.
Figure 4:
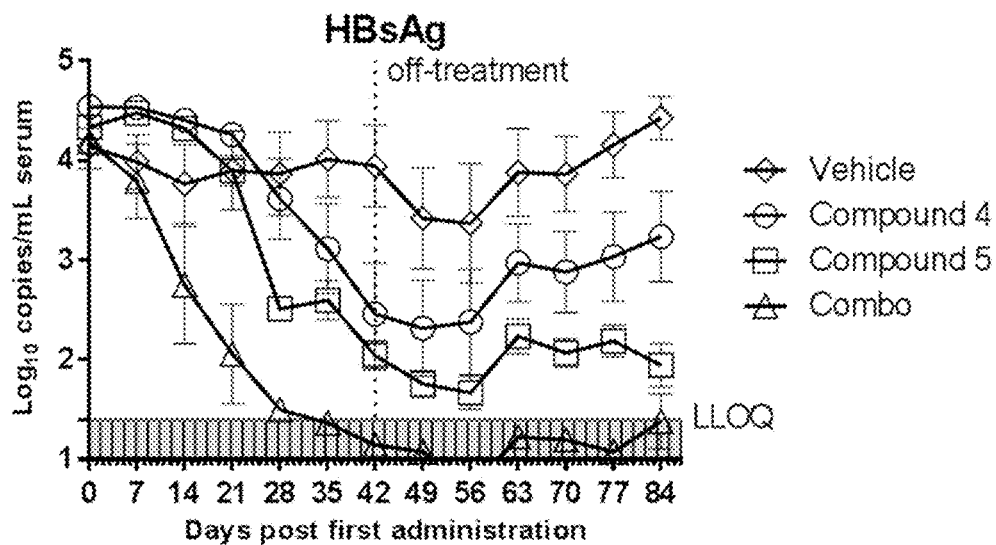
Figure 4:
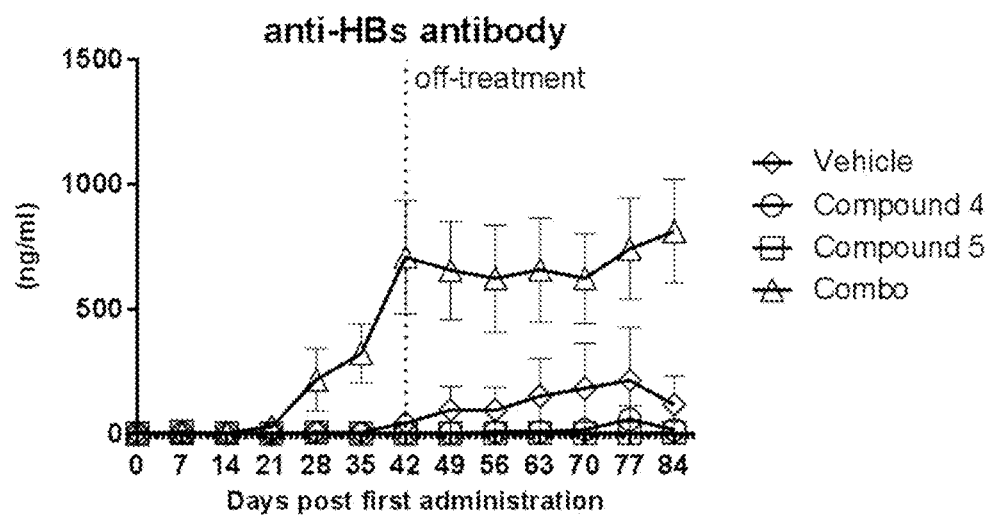

Note:
Tx Grp = Treatment group;
Vol = Volume;
p.o. = oral gavage;
QD = Once daily;
QOD = Every other day;
QW = Once weekly;
No. An = Number of animals As shown in FIG. 4, monotherapies of Compound 4 at 10 mg/kg QW and Compound 5 at 20 mg/kg QD by themselves resulted in significant reduction in HBV DNA and HBsAg after 42 days of treatment. Furthermore, the combination of Compound 4 and Compound 5 demonstrated even more antiviral benefit with greater HBsAg reduction. In all animals that received the combination therapy, HBsAg in serum was reduced to an undetectable level below the lower limit of quantification (LLOQ) after 42 days of the treatment, and such HBsAg loss was sustainable throughout the 42-day off-treatment period. Along with the HBsAg reduction, all these animals developed significantly higher levels of anti-HBs antibody than in other groups. At the end of the off-treatment period, B cells that were actively producing anti-HBs antibody were still detectable in spleens (shown in FIG. 4-D) from the animals that received the combination treatment. Therefore, such combination therapy has the potential to achieve HBsAg loss and anti-HBs seroconversion in chronically HBV infected patients.

Example 6

A Combination of TLR7 Agonist (Compound 3) and HBV Capsid Assembly Inhibitor (Compound 5) Potently Reduced HBV DNA and HBsAg in AAV-HBV Mouse Model The combination of Compound 3 and Compound 5, along with their monotherapies, was evaluated using the same AAV-HBV mouse model and the methods to measure HBV biomarkers as described in Example 5.

As shown in Table 3, a total of 24 mice were stratified into 4 groups for the study. In Group 01, animals were treated with Vehicle once daily (QD) for 42 days and served as the placebo control. In Group 02, Compound 3 was dosed once every other week (QOW) at 1 mg/kg for 42 days. Compound 5 was dosed once daily (QD) at 20 mg/kg for 42 days alone in Group 03, or in combination with 1 mg/kg of Compound 3 QOW in Group 04. All the test articles were administered by oral gavage (PO) with a total dose volume of 10 mL/kg. The 42-day treatment was followed by a 45-day off-treatment period. Animals were submandibularly bled once weekly for serum collection until the study end. The serum samples were subjected to the analysis of HBV biomarkers.

TABLE 3

Combination study design in AAV-HBV mouse model for Compound 3 and 5

| Tx Grp | Treatment | Dose (mg/kg) | Dose Vol (mL/kg) | Dose Route | Dose Schedule | No. An |
|---|---|---|---|---|---|---|
| 01 | Vehicle | 0 | 10 | p.o. | QD Days 0~41 | 6 |
| 02 | Compound 3 | 1 | 10 | p.o. | QOW Days 0~41 | 6 |
| 03 | Compound 5 | 20 | 10 | p.o. | QD Days 0~41 | 6 |
| 04 | Compound 3 and Compound 5 | 1 and 20 | 5 and 5 | p.o. and p.o. | QOW and QD Days 0~41 | 6 |

Figure 5:
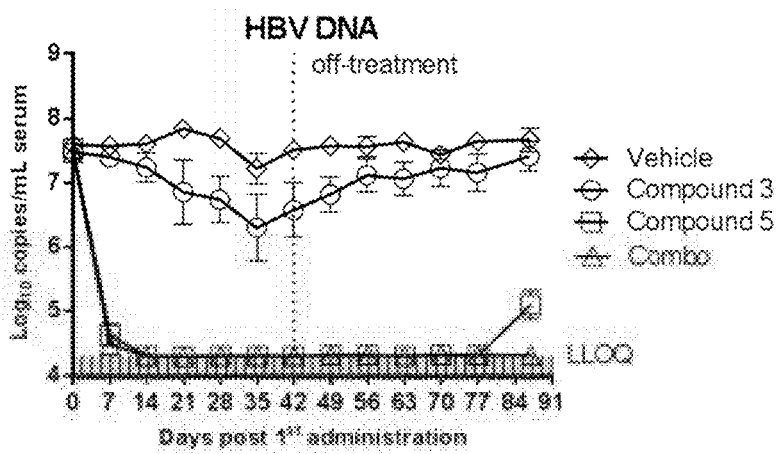
FIG. 5 shows the HBV DNA (FIG. 5A), HBsAg (FIG. 5B), and anti-HBs antibody level (FIG. 5C) of the AAV-HBV infected mice treated with Vehicle, 1 mg/kg of Compound 3 once every other week, 20 mg/kg of Compound 5 once daily, and combination therapy for 42 days followed by a 45-day off-treatment period. The results are presented as mean±SEM. LLOQ: lower limit of quantification.
Figure 5:
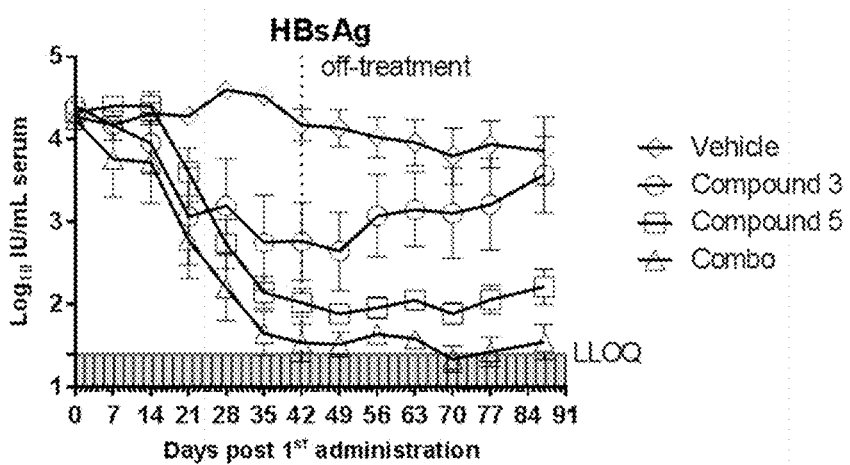
Figure 5:
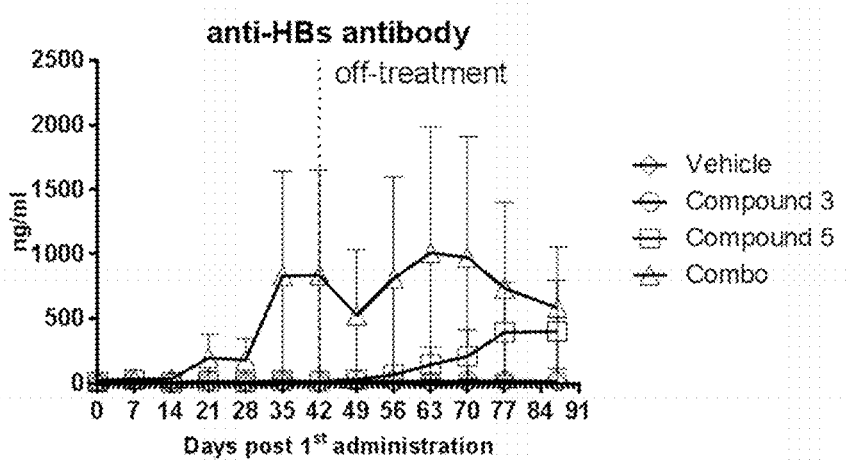

Abbreviations:
Tx Grp = Treatment group;
Vol = Volume;
p.o. = oral gavage;
QD = Once daily;
QOD = Every other day;
QW = Once weekly;
No. An = Number of animals As shown in FIG. 5, monotherapies of Compound 3 at 1 mg/kg QOW and Compound 5 at 20 mg/kg QD by themselves resulted in significant reduction in HBV DNA and HBsAg after 42 days of treatment. The combination of Compound 3 and Compound 5 demonstrated even more antiviral benefit with greater HBsAg reduction. In the group of the combination therapy, 4 out of 6 animals had undetectable levels of HBsAg in serum (below the LLOQ) after 42 days of the treatment, and such HBsAg loss was sustainable throughout the 45-day off-treatment period. Along with the HBsAg reduction, the group treated with combination therapy demonstrated significantly higher levels of anti-HBs antibody than other groups. Thus, such combination therapy has the potential to achieve HBsAg loss and anti-HBs seroconversion in chronically HBV-infected patients.

The invention claimed is:

1. A pharmaceutical composition comprising a TLR7 agonist and an HBV capsid assembly inhibitor, in a pharmaceutically acceptable carrier, wherein the TLR7 agonist is a compound of formula (I):

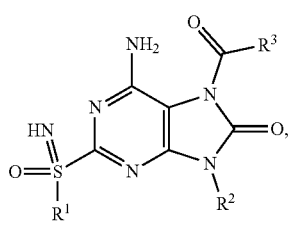

wherein:
R$^1$ is C$_{1-6}$alkyl;
R$^2$ is benzyl, said benzyl being unsubstituted or substituted by one, two or three substituents independently selected from halogen and C$_{1-6}$alkyl; and
R$^3$ is —NR$^4$R$^5$, wherein:
R$^4$ is C$_{1-6}$alkyl or C$_{1-6}$alkoxyC$_{1-6}$alkyl;
R$^5$ is (C$_{1-6}$alkyl)$_2$NCOOC$_{1-6}$alkyl, C$_{1-6}$alkoxyC$_{1-6}$alkyl, C$_{1-6}$alkoxycarbonyl(C$_{1-6}$alkyl)aminoC$_{1-6}$alkyl, C$_{1-6}$alkoxycarbonyl(phenyl)C$_{1-6}$alkyl, C$_{1-6}$alkoxycarbonylC$_{1-6}$alkyl, C$_{1-6}$alkoxycarbonyloxyC$_{1-6}$alkyl, C$_{1-6}$alkyl, C$_{1-6}$alkylcarbonyl(C$_{1-6}$alkyl)aminoC$_{1-6}$alkyl or pyrrolidinylcarbamoyloxyC$_{1-6}$alkyl; or
R$^4$ and R$^5$ together with the nitrogen they are attached to form a heterocyclyl; or a pharmaceutically acceptable salt, enantiomer or diastereomer thereof.

2. The pharmaceutical composition according to claim 1, wherein the TLR7 agonist is:

6-Amino-9-[(4-chlorophenyl)methyl]-2-[S(S)-ethylsulfonimidoyl]-N-methyl-8-oxo-N-propyl-purine-7-carboxamide;
6-Amino-9-[(4-chlorophenyl)methyl]-2-[S(R)-ethylsulfonimidoyl]-N-methyl-8-oxo-N-propyl-purine-7-carboxamide;
6-Amino-9-[(4-chlorophenyl)methyl]-N-ethyl-2[S(S)-ethylsulfonimidoyl]-N-methyl-8-oxo-purine-7-carboxamide; or
6-Amino-2-[S(R)-ethylsulfonimidoyl]-N-methyl-8-oxo-N-propyl-9-(p-tolylmethyl)purine- 7-carboxamide;
or a pharmaceutically acceptable salt, enantiomer or diastereomer thereof.

3. A pharmaceutical composition comprising a TLR7 agonist and an HBV capsid assembly inhibitor, in a pharmaceutically acceptable carrier, wherein the TLR7 agonist is a compound of formula (II):

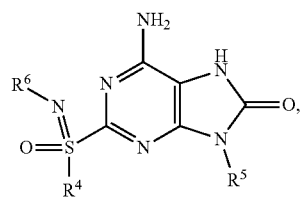

wherein:
R$^4$ is C$_{1-6}$alkyl, haloC$_{1-6}$alkyl, C$_{3-7}$cycloalkylC$_{1-6}$alkyl, C$_{1-6}$alkoxyC$_{1-6}$alkyl or pyrrolidinylC$_{1-6}$alkyl;
R$^5$ is C$_{1-6}$alkyl, phenylC$_{1-6}$alkyl, pyridinylC$_{1-6}$alkyl or pyrimidinylC$_{1-6}$alkyl, said phenylC$_{1-6}$alkyl, pyridinylC$_{1-6}$alkyl and pyrimidinylC$_{1-6}$alkyl are unsubstituted or substituted by one, two or three substituents independently selected from halogen, C$_{1-6}$alkyl, $C_{1-6}$alkoxy, cyano, carboxy, carbamoyl, halo$C_{1-6}$alkyl, $C_{1-6}$alkylsulfonyl, $C_{1-6}$alkoxycarbonyl, $C_{1-6}$alkoxy$C_{1-6}$ alkylaminocarbonyl, pyrrolidinylcarbonyl and piperidinylcarbonyl; and $R^6$ is H;

or a pharmaceutically acceptable salt, enantiomer or diastereomer thereof.

4. The pharmaceutical composition according to claim 3, wherein the TLR7 agonist is:

6-Amino-9-[(4-chlorophenyl)methyl]-2-(S(S)-ethylsulfonimidoyl)-7H-purin-8-one;

6-Amino-9-[(4-chlorophenyl)methyl]-2-(S(R)-ethylsulfonimidoyl)-7H-purin-8-one; or 6-Amino-2-(S(R)-ethylsulfonimidoyl)-9-(p-tolylmethyl)-7H-purin-8-one;

or a pharmaceutically acceptable salt, enantiomer or diastereomer thereof.

5. The pharmaceutical composition according to claim 1, wherein the HBV capsid assembly inhibitor is a compound of formula (III)

(III)

wherein:

$R^7$ is hydrogen, halogen or $C_{1-6}$alkyl;

$R^8$ is hydrogen or halogen;

$R^9$ is hydrogen or halogen;

$R^{10}$ is $C_{1-6}$alkyl;

$R^{11}$ is hydrogen, hydroxy$C_{1-6}$alkyl, aminocarbonyl, $C_{1-6}$alkoxycarbonyl or carboxy;

$R^{12}$ is hydrogen, $C_{1-6}$alkoxycarbonyl or carboxy-$C_mH_{2m}$—;

X is carbonyl or sulfonyl;

Y is —$CH_2$—, —O— or —N($R^{13}$)—, wherein $R^{13}$ is hydrogen, $C_{1-6}$alkyl, halo$C_{1-6}$alkyl, $C_{3-7}$cycloalkyl-$C_mH_{2m}$—, $C_{1-6}$alkoxycarbonyl-$C_mH_{2m}$—,—$C_tH_{2t}$—COOH, -halo$C_{1-6}$alkyl-COOH, —($C_{1-6}$alkoxy)$C_{1-6}$alkyl-COOH, —$C_{1-6}$alkyl-O—$C_{1-6}$alkyl-COOH, —$C_{3-7}$cycloalkyl-$C_mH_{2m}$—COOH, —$C_mH_{2m}$—$C_{3-7}$cycloalkyl-COOH, hydroxy-$C_tH_{2t}$—, carboxyspiro[3.3]heptyl, carboxyphenyl-$C_mH_{2m}$—, or carboxypyridinyl-$C_mH_{2m}$—;

W is —$CH_2$—, —$C(C_{1-6}alkyl)_2$—, —O— or carbonyl;

n is 0 or 1;

m is 0-7; and t is 1-7;

or a pharmaceutically acceptable salt, enantiomer or diastereomer thereof.

6. The pharmaceutical composition according to claim 5, wherein the HBV capsid assembly inhibitor is:

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

or a pharmaceutically acceptable salt, enantiomer or diastereomer thereof.

7. A pharmaceutical composition, wherein the composition consists of:

6-Amino-9-[(4-chlorophenyl)methyl]-2-[S(S)-ethylsulfonimidoyl]-N-methyl-8-oxo-N-propyl-purine-7-carboxamide and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-2-[S(S)-ethylsulfonimidoyl]-N-methyl-8-oxo-N-propyl-purine-7-carboxamide and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-2-[S(R)-ethylsulfonimidoyl]-N-methyl-8-oxo-N-propyl-purine-7-carboxamide and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-2-[S(R)-ethylsulfonimidoyl]-N-methyl-8-oxo-N-propyl-purine-7-carboxamide and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-N-ethyl-2[S(S)-ethylsulfonimidoyl]-N-methyl-8-oxo-purine-7-carboxamide and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-N-ethyl-2[S(S)-ethylsulfonimidoyl]-N-methyl-8-oxo-purine-7-carboxamide and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-2-[S(R)-ethylsulfonimidoyl]-N-methyl-8-oxo-N-propyl-9-(p-tolylmethyl)purine-7-carboxamide and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-2-[S(R)-ethylsulfonimidoyl]-N-methyl-8-oxo-N-propyl-9-(p-tolylmethyl)purine-7-carboxamide and 3-[(8aS)-7-[[(4R)-4-(2-chloro-3-fluoro-phenyl)-5-ethoxycarbonyl-2-thiazol-2-yl-1,4-dihydropyrimidin- 6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-2-(S(S)-ethylsulfonimidoyl)-7H-purin-8-one and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-2-(S(S)-ethylsulfonimidoyl)-7H-purin-8-one and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-2-(S(R)-ethylsulfonimidoyl)-7H-purin-8-one and 3-[(8aS)-7-[[(4S)-5-ethoxycarbonyl-4-(3-fluoro-2-methyl-phenyl)-2-thiazol-2-yl-1,4-dihydropyrimidin-6-yl]m ethyl]-3-oxo-5,6,8,8a-tetrahydro-1H-imidazo[1,5-a]pyrazin-2-yl]-2,2-dimethyl-propanoic acid;

6-Amino-9-[(4-chlorophenyl)methyl]-2-(S(R)-ethylsulfonimidoyl)-7H-purin-8-one and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

6-Amino-2-(S(R)-ethylsulfonimidoyl)-9-(p-tolylmethyl)-7H-purin-8-one and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or 6-Amino-2-(S(R)-ethylsulfonimidoyl)-9-(p-tolylmethyl)-7H-purin-8-one and 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

in a pharmaceutically acceptable carrier.

8. The pharmaceutical composition according to claim 1, wherein the composition consists of:

6-Amino-9-[(4-chlorophenyl)methyl]-N-ethyl-2[S(S)-ethylsulfonimidoyl]-N-methyl-8-oxo-purine-7-carboxamide and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or 6-Amino-2-[S(R)-ethylsulfonimidoyl]-N-methyl-8-oxo-N-propyl-9-(p-tolylmethyl)purine-7-carboxamide and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

in a pharmaceutically acceptable carrier.

9. The pharmaceutical composition according to claim 1, wherein the composition additionally comprises one or more other antiviral agents.

10. The pharmaceutical composition according to claim 9, wherein said one or more other antiviral agents are selected from lamivudine, adefovir, tenofovir, telbivudine and entecavir.

11. The pharmaceutical composition according to claim 3, wherein the HBV capsid assembly inhibitor is a compound of formula (III)

(III)

wherein:
$R^7$ is hydrogen, halogen or $C_{1-6}$alkyl;
$R^8$ is hydrogen or halogen;
$R^9$ is hydrogen or halogen;
$R^{10}$ is $C_{1-6}$alkyl;
$R^{11}$ is hydrogen, hydroxy$C_{1-6}$alkyl, aminocarbonyl, $C_{1-6}$alkoxycarbonyl or carboxy;
$R^{12}$ is hydrogen, $C_{1-6}$alkoxycarbonyl or carboxy-$C_mH_{2m}$—;
X is carbonyl or sulfonyl;
Y is —CH$_2$—, —O— or —N(R$^{13}$)—,
wherein $R^{13}$ is hydrogen, $C_{1-6}$alkyl, halo$C_{1-6}$alkyl, $C_{3-7}$cycloalkyl-$C_mH_{2m}$—, $C_{1-6}$alkoxycarbonyl-$C_mH_{2m}$—, —$C_tH_{2t}$—COOH, -halo$C_{1-6}$alkyl-COOH, —($C_{1-6}$alkoxy)$C_{1-6}$alkyl-COOH, —$C_{1-6}$alkyl-O—$C_{1-6}$alkyl-COOH, -$C_{3-7}$cycloalkyl-$C_mH_{2m}$—COOH, —$C_mH_{2m}$-$C_{3-7}$cycloalkyl-COOH, hydroxy-$C_tH_{2t}$—, carboxyspiro[3.3]heptyl, carboxyphenyl-$C_mH_{2m}$—, or carboxypyridinyl-$C_mH_{2m}$—;
W is —CH$_2$—, —C($C_{1-6}$alkyl)$_2$—, —O— or carbonyl;
n is 0 or 1;
m is 0-7; and
t is 1-7;
or a pharmaceutically acceptable salt, enantiomer or diastereomer thereof.

12. The pharmaceutical composition according to claim 11, wherein the HBV capsid assembly inhibitor is:

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; or 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

or a pharmaceutically acceptable salt, enantiomer or diastereomer thereof.

13. The pharmaceutical composition according to claim 3, wherein the composition additionally comprises one or more other antiviral agents.

14. The pharmaceutical composition according to claim 13, wherein the one or more other antiviral agents are selected from lamivudine, adefovir, tenofovir, telbivudine and entecavir.

* * * * *